(12) United States Patent
Wilson et al.

(10) Patent No.: US 7,202,252 B2
(45) Date of Patent: Apr. 10, 2007

(54) $A_1$ ADENOSINE RECEPTOR ANTAGONISTS

(75) Inventors: Constance Neely Wilson, Research Triangle Park, NC (US); John J. Partridge, Chapel Hill, NC (US)

(73) Assignee: Endacea, Inc., Raleigh, NC (US)

( * ) Notice: Subject to any disclaimer, the term of this patent is extended or adjusted under 35 U.S.C. 154(b) by 177 days.

(21) Appl. No.: 10/780,296

(22) Filed: Feb. 17, 2004

(65) Prior Publication Data

US 2005/0119258 A1 Jun. 2, 2005

Related U.S. Application Data

(60) Provisional application No. 60/448,212, filed on Feb. 19, 2003.

(51) Int. Cl.
*C07D 473/06* (2006.01)
*C07D 473/04* (2006.01)
*A61K 31/522* (2006.01)
*A61P 37/02* (2006.01)
*A61P 11/06* (2006.01)

(52) U.S. Cl. .............................. 514/263.2; 514/263.21; 514/263.22; 514/263.23; 514/263.34; 514/263.35; 514/263.36; 544/267; 544/269; 544/270; 544/272; 544/273; 544/311; 544/312; 558/392

(58) Field of Classification Search ................ 544/267, 544/269, 270, 272, 273; 514/263.2, 263.21, 514/263.22, 263.23, 263.34, 263.35, 263.36
See application file for complete search history.

(56) References Cited

U.S. PATENT DOCUMENTS

| | | | |
|---|---|---|---|
| 2,840,559 A * | 6/1958 | Krantz, Jr. et al. ......... 544/272 |
| 2,887,486 A | 5/1959 | Leake et al. |
| 3,031,451 A | 4/1962 | Schlesinger et al. |
| 3,309,271 A | 3/1967 | Georges et al. |
| 3,317,533 A | 5/1967 | De Ridder |
| 3,961,060 A | 6/1976 | Fuxe |
| 4,092,417 A | 5/1978 | Credner et al. |
| 4,299,832 A | 11/1981 | Brown et al. |
| 4,378,359 A | 3/1983 | Chiodoni et al. |
| 4,548,818 A | 10/1985 | Kjellin et al. |
| 4,612,315 A | 9/1986 | Jacobson et al. |
| 4,622,324 A | 11/1986 | Klessing et al. |
| 4,696,932 A | 9/1987 | Jacobson et al. |
| 4,769,377 A | 9/1988 | Snyder et al. |
| 4,772,607 A | 9/1988 | Badger et al. |
| 4,868,186 A | 9/1989 | Franzone et al. |
| 4,879,296 A | 11/1989 | Daluge et al. |
| 4,968,672 A | 11/1990 | Jacobson et al. |
| 4,971,972 A | 11/1990 | Doll et al. |
| 5,032,593 A | 7/1991 | Rzeszotarski et al. |
| 5,066,655 A | 11/1991 | Olsson |
| 5,068,236 A | 11/1991 | Suzuki et al. |
| 5,208,240 A | 5/1993 | Peet et al. |
| 5,248,770 A | 9/1993 | Jacobson et al. |
| 5,256,650 A | 10/1993 | Peet et al. |
| 5,290,782 A * | 3/1994 | Suzuki et al. .......... 514/263.34 |
| 5,296,463 A | 3/1994 | Lee et al. |
| 5,298,508 A | 3/1994 | Jacobson et al. |
| 5,314,890 A | 5/1994 | Agostini et al. |
| 5,340,813 A | 8/1994 | Klein et al. |
| 5,395,836 A | 3/1995 | Shimada et al. |
| 5,434,150 A | 7/1995 | Austel et al. |
| 5,447,933 A | 9/1995 | Suzuki et al. |
| 5,504,090 A | 4/1996 | Neely |
| 5,532,368 A | 7/1996 | Kufner-Muhl et al. |
| 5,543,415 A | 8/1996 | Suzuki et al. |
| 5,545,627 A | 8/1996 | Jacobson et al. |
| 5,714,494 A * | 2/1998 | Connell et al. ........ 514/263.23 |
| 5,719,279 A | 2/1998 | Kufner-Muhl et al. |
| 5,733,916 A | 3/1998 | Neely |
| 5,739,331 A * | 4/1998 | Thyrion et al. ............. 544/272 |
| 5,786,360 A | 7/1998 | Neely |

(Continued)

FOREIGN PATENT DOCUMENTS

BE      636 828 A      3/1964

(Continued)

OTHER PUBLICATIONS

Belardinelli et al., *1, 3-Dipropyl-8-[2-(5, 6-Epoxy)Norbornyl] Xanthine, a Potent Specific and Selective $A_1$ Adenosine Receptor Antagonist in the Guinea Pig Heart and Brain and in DDT $_1$MF-2 Cells*, The Journal of Pharmacology and Experimental Therapeutics, vol. 276, No. 2:1167-1176 (1995).

Beauglehole et al., *New Irreversible Adenosine $A_1$ Antagonists Based on FSCPX*, Bioorganic and Medicinal Chemistry Letters, 12:3179-3182 (2002).

Beauglehole et al., *Fluorosulfonyl-Substituted Xanthines as Selective Irreversible Antagonists for the $A_1$-Adenosine Receptor*, J. Med. Chem. 43:4973-4980 (2000).

(Continued)

*Primary Examiner*—Mark L. Berch
(74) *Attorney, Agent, or Firm*—Alston & Bird LLP

(57) ABSTRACT

Compounds of the general formula (I) are described:

(I)

$$R_1-N \cdots NH \cdots (CH_2)_q-A-R_3$$
$$R_2$$

wherein A is a 5- or 6-membered aromatic or heteroaromatic ring. Compositions comprising such compounds and methods of use thereof are also described.

17 Claims, No Drawings

U.S. PATENT DOCUMENTS

| | | | |
|---|---|---|---|
| 5,932,557 A | 8/1999 | Mustafa et al. | |
| 6,001,842 A | 12/1999 | Neely | |
| 6,117,445 A | 9/2000 | Neely | |
| 2002/0058667 A1 | 5/2002 | Castelhano et al. | |
| 2002/0082269 A1 | 6/2002 | Neely | |
| 2002/0111333 A1 | 8/2002 | Lin et al. | |
| 2003/0212082 A1 | 11/2003 | Linden et al. | |
| 2004/0014766 A1 | 1/2004 | Dunten et al. | |
| 2004/0110774 A1 | 6/2004 | Wilson | |
| 2005/0187226 A1* | 8/2005 | Wilson et al. | 514/263.2 |

FOREIGN PATENT DOCUMENTS

| | | |
|---|---|---|
| DE | 1 245 383 | 7/1967 |
| DE | 26 59 241 | 7/1978 |
| EP | 0 501 379 A2 | 9/1992 |
| EP | 0 503 563 A2 | 9/1992 |
| EP | 0 764 647 A1 | 3/1997 |
| FR | 2 483 922 | 11/1981 |
| GB | 947495 | 1/1964 |
| JP | 9216883 A | 8/1997 |
| WO | WO 98/03507 | 1/1998 |
| WO | WO 99/67239 A1 | 12/1999 |
| WO | WO 01/34610 A1 | 5/2001 |
| WO | WO 2003/028730 A2 | 4/2003 |
| WO | WO 03/028730 A2 | 10/2003 |
| WO | WO 2004/074247 A2 | 9/2004 |
| WO | WO 2004/110379 A2 | 12/2004 |
| WO | WO 2004110379 A2 * | 12/2004 |

OTHER PUBLICATIONS

Sonja Hess, *Recent Advances in Adenosine Receptor Antagonist Research*, Expert Opinion, Ashley Publications, 1354-3776 (2001).

Jacobson et al., *Adenosine Receptors: Pharmacology, Structure-Activity Relationships; and Therapeutic Potential*, Journal of Medicinal Chemistry, vol. 35, No. 3:407-422 (Feb. 7, 1992).

Kuroda et al., *Design, Synthesis and Biological Evaluation of a Novel Series of Potent, Orally Active Adenosine $A_1$ Receptor Antagonists with High Blood-Brain Barrier Permeability*, Chem. Pharm. Bull., 49:988-998 (2001).

Nicot et al., *High-Performance Liquid Chromatographic Method for the Determination of Bamifylline and it's Three Metabolites in Human Plasma*, Journal of Chromatography, 277:239-249 (1983).

Novellino et al., *Design, Synthesis and Biological Evaluation of Novel N-Alkyl-and N-Acyl-(7-substituted-2-2phenylimidazo[1.2-a] [1,3,5] triaxzin-4-yl] amines (ITAs) as Novel $A_1$ Adenosine Receptor Antagonists*, J. Med. Chem. 45:5030-5036 (2002).

Sacchi et al., *Research on Heterocyclic Compounds. Part XXXVI. Imidazo[1,2-a]pyrimidine-a-acetic derivatives: synthesis and anti-inflammatory activity*, Eur. J. Med. Chem., 32:677-682 (1997).

Scammells et al., *Substituted 1,3-Dipropylxanthines as Irreversible Antagonists of $A_1$ Adenosine Receptors*, J. Med. Chem. 37:2704-2712 (1994).

Van Muijlwijk-Koezen et al., *Synthesis and Use of FSCPX, an Irreversible Adenosine $A_1$ Antagonist, as a 'Receptor Knock-Down' Tool*, Bioorganic & Medicinal Chemistry Letters, 11:815-818 (2001).

Van Galen et al., *A Model for the Antagonist Binding Site on the Adenosine $A_1$ Receptor, Based on Steric, Electrostatic, and Hydrophobic Properties*, J. Med. Chem., 33:1708-1713 (1990).

Van Tilburg et al., *Subsituted 4-Phenyl-2-2(phenylcarboxamido)-1,3-thiazole Derivatives as Antagonists for the Adenosine $A_1$ Receptor*, Bioorganic & Medicinal Chemistry Letters, 11:2017-2019 (2001).

Wilson et al., *Lipopolysaccaride Binds to and Activates $A_1$ Adenosine Receptors on Human Pulmonary Artery Endothelial Cells*, Journal of Endotoxin Research, vol. 8, No. 4:263-271 (2002).

Poulsen, Bioorganic & Medicinal Chem. Let, 6,619 (1998).

Foley, L.H. et al., "Modified 3-Alkyl-1, 8-dibenzylxanthines as GTP-Competitive Inhibitors of Phosphoenolpyruvate Carboxykinase," *Bioorganic & Medicinal Chemistry Letters*, 2003, pp. 3607-3610, vol. 13.

Abbracchio, M.P. and F. Cattabeni, "Selective Activity of Bamifylline on Adenosine $A_1$-Receptors in Rat Brain," *Pharmacological Research Communications*, 1987, pp. 537-545, vol. 19(8).

Belliardo, F. and C. Lucarelli, "Micro-Scale Liquid Chromatographic Method for the Determination of Bamifylline and its Major Metabolite in Human Plasma," *Journal of Chromatography*, 1990, pp. 305-309, vol. 535.

Carlucci, G., et al., "Determination of Bamifylline Hydrochloride Impurities in Bulk Material and Pharmaceutical Forms Using Liquid Chromatography with Ultraviolet Detection," *Journal of Pharmaceutical & Biomedical Analysis*, 1990, pp. 1067-1069, vol. 8.

Jacobson, K.A., et al., "A Functionalized Congener Approach to Adenosine Receptor Antagonists: Amino Acid Conjugates of 1,3-Dipropylxanthine," *Molecular Pharmacology*, 1985, pp. 126-133, vol. 29.

Jacobson, K.A., et al., "Electrophilic Derivatives of Purines as Irreversible Inhibitors of $A_1$ Adenosine Receptors," *Journal of Medicinal Chemistry*, 1989, pp. 1043-1051, vol. 32.

Jacobson, K.A., et al., "Molecular Probes for Extracellular Adenosine Receptors," *Biochemical Pharmacology*, 1987, pp. 1697-1707, vol. 36(10).

Müeller, C.E., et al., "7-Deaza-2-phenyladenines: Structure-Activity Relationships of Potent $A_1$ Selective Adenosine Receptor Antagonists," 1990, pp. 2822-2828, vol. 33(10).

Neely, C.F., et al., "$A_1$ Adenosine Receptor Antagonists Block Ischemia-Reperfusion Injury of the Heart," *AHA-Circulation*, Nov. 1996, pp. 1-5, 94(9).

Patel, A. et al., "I-BW-A844U, an Antagonist Radioligand with High Affinity and Selectivity for Adenosine $A_1$ Receptors, and $^{125}$I-Azido-BW-A844U, a Photoaffinity Label," *Molecular Pharmacology*, 1988, pp. 585-591, vol. 33.

Poulsen, S-A and R.J. Quinn, "Adenosine Receptors: New Opportunities for Future Drugs," *Bioorganic & Medicinal Chemistry*, 1998, pp. 619-641, vol. 6.

Schiantarelli, P., et al., "Evidence of Pulmonary Tropism of Bamifylline and its Main Active Metabolite," *Arzneim.-Forsch/Drug Res.*, 1989, pp. 215-219, vol. 39.

Van Galen, P.J.M., "Adenosine $A_1$ and $A_2$ Receptors: Structure-Function Relationships," *Medicinal Research Reviews*, 1992, pp. 423-471, vol. 12.

Van Rhee, A.M., et al., "Tetrahydrobenzothiophenone Derivatives as a Novel Class of Adenosine Receptor antagonists," *J. Med. Chem.*, 1996, pp. 398-406, vol. 39(2).

Windholz, M., ed., "Bamethan," *The Merck Index*, 1983, p. 138, Tenth Edition, Merck & Co., Inc., Rahway, N.J.

"Communications to the Editor," *J. Med. Chem.*, 1992, pp. 3578-3581, vol. 35(19).

"Other News to Note," *BioWorld Today*, Mar. 1996, p. 2.

Ali, et al., "Adenosine-Induced Bronchoconstriction and Contraction of Airway Smooth Muscle from Allergic Rabbits with Late-Phase Airway Obstruction: Evidence for an Inducible Edenosine $A_1$ Receptor," *The Journal of Pharmacology and Experimental Therapeutics*, 1993, pp. 1328-1334, vol. 268(3).

Angulo, et al., "$A_1$ Adenosine Receptors Accumulate in Neurodegenerative Structures in Alzheimer Disease and Mediate Both Amyloid Precursor Protein Processing and Tau Phosphorylation and Translocation," *Brain Pathol.* 2003, -pp. 440-451.

Aslanian, et al., "Cardiovascular and Pulmonary Diseases," *Annual Reports in Medicinal Chemistry*, 2001, pp. 32-40, vol. 36(II), Academic Press, San Diego, CA.

Ball, et al., "Clinical Potential of Respirable Antisense Oligonucleotides (RASONs) in Asthma," *Am. J. Pharmacogenomics*, 2003, pp. 97-106, vol. 3(2).

Berti, et al., "Pharmacological Activity of Bamifylline on Lung Anaphylaxis: In Vitro Studies," *Pharmacological Research*, 1990, vol. 22(2).

Cronstein, et al., "Neutrophil Adherence to Endothelium is Enhanced Via Adenosine $A_1$ Receptors and Inhibited Via Adenosine $A_2$ Receptors," *The Journal of Immunology*, 1992, pp. 2201-2206, vol. 148.

Cronstein, et al., "The Adenosine/Neutrophil Paradox Resolved: Human Neutrophils Possess Both A1 and A2 Receptors that Promote Chemotaxis and Inhibit $O_2$ Generation, Respectively," *J Clinic. Invest.*, 1990, pp. 1150-1157, vol. 85.

Dar, M.S. et al., "Acute Ethanol / Cannabinoid-Induced Ataxia and Its Antagonism by Oral/Systemic/Intracerebellar $A_1$ Adenosine Receptor Antisense in Mice," *Brain Research*, 2002, pp. 53-60, vol. 957.

Forman, et al., "Sustained Reduction in Myocardial Reperfusion Injury with an Adenosine Receptor Antagonist: Possible Role of the Neutrophil Chemoatractant Response," *The Journal of Pharmacology and Experimental Therapeutics*, 2000, pp. 929-938, vol. 292(3).

Gaspardone, et al., "Bamiphylline Improves Exercise-Induced Myocardial Ischernia Through a Novel Mechanism of Action," *Circulation*, 1993, pp. 502-508, vol. 88(2).

Gaubert, Yves, "Clinical Experience with a New Antispasmodic," *Journal De Medicine De Bordeaux*, May 1967, pp. 772-776, vol. 5.

Gottlieb, S.S., et al., "BG9719 (CVT-124), an $A_1$ Adenosine Receptor antagonist, Protects Against the Decline in Renal Function Observed with Diuretic Therapy," *Journal of American Heart Association*, 2002, pp. 1348-1353.

Marone, G., et al., "Adenosine Receptors on Human Leukocytes IV. Characterization of an $A_1/R_i$ Receptor," *Int. J. Clin. Lab. Res.*, 1992, pp. 235242, vol. 22.

Marone, G., et al., "Adenosine Receptors on Human Inflammatory Cells[1]," *Int. Archs Allergy appl. Immun.*, 1985, pp. 259-263, vol. 77.

Mayne, M., et al., Dysregulation of Adenosine A1 Receptor-Mediated Cytokine Expression in Peripheral Blood Mononuclear Cells from Multiple Sclerosis Patients, *American Neurological Association*, 1999, pp. 633-639.

Neely, C.F. et al., "$A_1$ Adenosine Receptor Antagonists Block Ischemia-Reperfusion Injury of the Lung," *American Physiological Society*, 1995, pp. L1036-L1046.

Neely, C.F. et al., "$A_1$ Adenosine Receptor Antagonists Block Ischemia-Reperfusion Injury of the Heart," *American heart Association, Inc.*, 1996, pp. II-376-II-380.

Neely, C.F. et al., "$A_1$ Adenosine Receptor Antagonists Block Endotoxin-Induced Lung Injury," *American Physiological Society*, 1997, pp. L353-L361.

McCoy, D.E., et al., "Identification and Function of $A_1$ Adenosine Receptors in Normal and Cyctic Fibrosis Human Airway Epithelial Cells," *American Physiological Society*, 1995, pp. C1520-C1527.

Obiefuna, P.C.M., et al., "A Novel $A_1$ Adenosine Receptor Antagonist, L-97-1 [3-[2-(4-Aminophenyl)-ethyl]-8-benzyl-7-{2-ethyl-(2-hydroxy-ethyl)-amino-ethyl}-1-propyl-3,7-dihydro-purine-2,6-dione], Reduces Allergic Responses to House Dust Mite in an Allergic Rabbit Model of Asthma," *The Journal of Pharmacology and*.

Panther, E., et al., "Expression and Function of Adenosine Receptors in Human Dendritic Cells," *The FASEB Journal*, 2001, pp. 1963-1970, vol. 15.

Salmon, J.E., et al., "Human Mononuclear Phagocytes Express Adenosine $A_1$ Receptors," *The Journal of Immunology*, 1993, pp. 2775-2785.

Santos, J.M., et al. "Clinical Experimentation with AC3810 (Trentadil)," *Publicado en la Revista Medicina*, Aug. 1964, vol. 8.

Satoh, A., et al., "Activation of Adenosine $A_1$ -Receptor Pathway Induces Edema Formation in the Pancreas of Rats," *American Gastroenterological Association*, 2000, pp. 829-836, vol. 119.

Varani, K., et al., "Alteration of Adenosine Receptors in Patients with Chronic Obstructive Pulmonary Disease," *Am J. Respir Crit Care Med*, 2005, pp. 398-406, vol. 173.

Weisberg, S.P., et al., "Adenosine Receptor Antagonists Inhibit the Development of Morphine Sensitization in the C57BL/6 Mouse," *Neucroscience Letters*, 1999, pp. 89-92.

Wilson, C.N., et al., "Lipopolysaccharide Binds to and Activates $A_1$ Adenosine Receptors on human Pulmonary Artery Endothelial Cells," *Journal of Endotaxin Research*, 2002, pp. 1-9, vol. 8.

* cited by examiner

$A_1$ ADENOSINE RECEPTOR ANTAGONISTS

RELATED APPLICATIONS

This application claims the benefit of U.S. provisional patent application Ser. No. 60/448,212, filed Feb. 19, 2003, the disclosure of which is incorporated by reference herein in its entirety.

FIELD OF THE INVENTION

The present invention concerns compounds useful as $A_1$ adenosine receptor antagonists, along with methods of use thereof.

BACKGROUND OF THE INVENTION

Adenosine receptors are involved in a vast number of peripheral and central regulatory mechanisms such as, for example, vasodilation, cardiac depression, inhibition of lipolysis, inhibition of insulin release and potentiation of glucagon release in the pancreas, and inhibition of neurotransmitter release from nerve endings.

In general, adenosine receptors can be divided into two main classes, $A_1$ receptors which can inhibit, and $A_2$ receptors which can stimulate adenylate cyclase activity. One of the best known classes of adenosine receptor antagonists are the xanthines which include caffeine and theophylline. See e.g., Müller et al., J. Med. Chem. 33: 2822–2828 (1990). In general, many of these antagonists often suffer from poor water solubility, and low potency or lack of selectivity for adenosine receptors. Additionally, selective analogues of adenosine receptor antagonists have been developed through the "functionalized congener" approach. Analogues of adenosine receptor ligands bearing functionalized chains have been synthesized and attached covalently to various organic moieties such as amines and peptides. Attachment of the polar groups to xanthine congeners has been found to increase water solubility. Nonetheless, such developments have yet to fully address problems associated with potency and selectivity. More recently Jacobson et al. J. Med. Chem. 35: 408–422 (1992) has proposed various derivatives of adenosine and theophylline for use as receptor antagonists. The article discloses that hydrophobic substituents are able to potentially enhance affinity. However, it is also acknowledged that such substituents may result in a decrease in solubility thus rendering the antagonists less soluble in vivo. In confronting these problems, Jacobson et al. indicates that a dipropyl substitution at the 1 and 3 positions of theophylline allows desirable affinity at $A_1$ receptors. It is also stated that substitutions at the 7-position are typically not favorable.

Selective analogues of adenosine receptor antagonists have been developed through the "functionalized congener" approach. See e.g., U.S. Pat. No. 4,968,672 to Jacobson et al.; and Jacobson et al., Mol. Pharmacol. 29: 126–133 (1985). In terms of pharmacology, the compounds advantageously display increased affinity at $A_1$ receptor sites relative to former $A_1$ receptor antagonists while simultaneously exhibiting good water solubility.

U.S. Pat. No. 5,786,360 to Neely describes $A_1$ adenosine receptor antagonists.

U.S. Pat. No. 6,489,332 to Neely describes $A_1$ adenosine receptor antagonists.

U.S. Pat. No. 5,719,279 to Kufner-Muhl et al. describes certain xanthine derivatives that have $A_1$ adenosine receptor affinity.

It is an object of the present invention to provide additional compounds useful as $A_1$ adenosine receptor antagonists, preferably compounds with good water solubility.

SUMMARY OF THE INVENTION

In one aspect, the present invention provides a compound of the general formula (I) or (more particularly) formula (II):

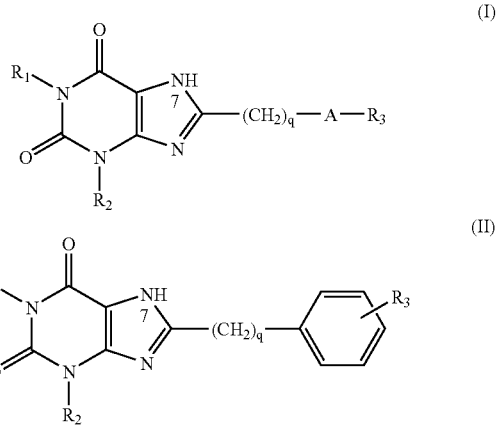

wherein:

A is a 5 or 6 membered aromatic or heteroaromatic ring containing 0 to 4 heteroatoms selected from the group consisting of N, O and S;

$R_1$ and/or $R_2$ are water-soluble groups or other groups as described below;

$R_3$ is selected from the group consisting of H, $NH_2$, $R_{15}COOH$, wherein $R_{15}$ is an alkyl or alkylidene group having 1 to 8 carbon atoms, and $(CH_2)_tOH$, wherein t is an integer ranging from 1 to 8; halides such as chloro, bromo, iodo or fluoro, substituted amines such as $NHR_8$, $NR_8R_9$, substituted amides such as $NHCOR_8$, and $NR_8COR_9$ as well as water-solubilizing groups $SO_3H$ and $PO_3H_2$; and q is an integer ranging from 1 to 8, preferably 1 to 5, and most preferably 1 to 3.

In a second aspect, the invention provides for assay-type probes of the above compound, wherein the probes are marked or conjugated with a detectable group such as a radioactive or non-radioactive detectable group.

In a third aspect, the invention provides a pharmaceutically acceptable salt of the above compound.

In a fourth aspect, the invention provides a pharmaceutical composition which comprises the above compound or its pharmaceutically acceptable salt in combination with a pharmaceutically acceptable carrier.

A further aspect of the present invention is a method of treating A1-adenosine receptor related disorders, AIDS and immune deficiency disorders, asthma, other inflammatory medical conditions and still other medical conditions in a subject in need thereof, comprising administering a compound as described herein (e.g., by inhalation or oral administration) to said subject in an amount effective to treat the said condition.

In a further aspect, the present invention provides for the use of compounds as described above for the preparation of a medicament for treating a disease in which antagonism of the $A_1$ adenosine receptor produces the desired effect.

Compounds of the present invention may further be used as described in C. Wilson, PCT Application WO 03/103675 (published Dec. 18, 2003).

DETAILED DESCRIPTION OF THE PREFERRED EMBODIMENTS

The present invention will now be described more fully hereinafter, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

While the present invention is intended primarily for the treatment of human subjects, it will be appreciated that other subjects, particularly mammalian subjects such as dogs, cats, horses, rabbits, etc., can also be treated by the methods of the present invention for veterinary purposes.

"Halogen" as used herein refers to any suitable halo group, such as fluorine, chlorine, bromine, and iodine.

As noted above, the present invention is directed to a compound of formula (I) or (II), or a pharmaceutically acceptable salt thereof:

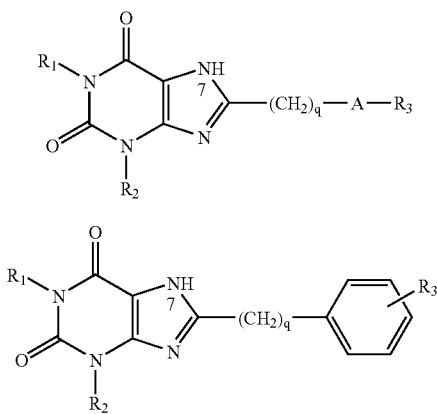

wherein:

A is a 5- or 6-membered aromatic or heteroaromatic ring containing 0 to 4 heteroatoms selected from the group consisting of N, O and S;

$R_1$ is a water-soluble group as set forth below (or H, or in some embodiments is $C_1$–$C_8$ alkyl); and $R_2$ is of the formula (i) or (ii):

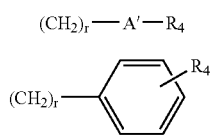

wherein:

A' is a 5- or 6-membered aromatic or heteroaromatic ring containing 0 to 4 heteroatoms selected from the group consisting of N, O and S;

r is an integer ranging from 1 to 20; preferably 2 to 12 and most preferably 2 to 10 or in an alternate embodiment $R_2$ is a water-soluble group as defined below;

$R_4$ is selected from the group consisting of H; $NH_2$; $(CH_2)_sOH$, wherein s is an integer ranging from 1 to 8; $R_{14}COOH$, wherein $R_{14}$ is an alkyl or alkylidene group having 1 to 8 carbon atoms; halides such as chloro, bromo, iodo or fluoro, substituted amines such as $NHR_8$, $NR_8R_9$, substituted amides such as $NHCOR_8$, and $NR_8COR_9$ as well as water-solubilizing groups $SO_3H$ and $PO_3H_2$; and $R_3$ is selected from the group consisting of H, $NH_2$, $R_{15}COOH$, wherein $R_{15}$ is an alkyl or alkylidene group having 1 to 8 carbon atoms, and $(CH_2)_tOH$, wherein t is an integer ranging from 1 to 8; halides such as chloro, bromo, iodo or fluoro, substituted amines such as $NHR_8$, $NR_8R_9$, substituted amides such as $NHCOR_8$, and $NR_8COR_9$ as well as water-solubilizing groups $SO_3H$ and $PO_3H_2$.

q is an integer ranging from 1 to 8, preferably 1 to 5, and most preferably 1 to 3.

As noted above, $R_1$ and/or $R_2$ may be water-soluble groups or other groups in which $R_1$ and/or $R_2$:

denote a $C_1$–$C_8$ alkanyl group, $C_2$–$C_8$ alkenyl group or $C_2$–$C_8$ alkynyl group which is optionally substituted by —CN, —$CH_2NR_6R_7OH$ (multiple substitution also being possible), —$OR_8$, —$NR_6R_7$, —$NHCOR_8$, —$NHCONR_6R_7$, halogen, —$OCOR_8$, —$OCH_2COOH$, —$OCH_2COOR_8$, —$SO_2R_5$, —S—$R_5$, —NHCONH phenyl, —$OCH_2$—$CONR_6R_7$, —$OCH_2CH_2OH$, —$SO_2$—$CH_2$—$CH_2$—O—$COR_8$, —$OCH_2$—$CH_2$—$NR_6R_7$, —$SO_2$—$CH_2$—$CH_2$—OH, —$CONHSO_2R_8$, —$CH_2CONHSO_2R_8$, —$OCH_2CH_2OR_8$, —COOH, —$COOR_8$, —$CONR_6R_7$, —CHO, —$SR_8$, —$SOR_8$, —$SO_2R_8$, —$SO_3H$, —$SO_2NR_6R_7$, —$OCH_2$—$CH_2OCOR_8$, —CH=NOH, —CH=$NOR_8$, —$COR_9$, —$CH(OH)R_9$, —$CH(OR_8)_2$, —CH=CH—$R_{10}$, —$OCONR_6R_7$, —$PO_3H_2$,

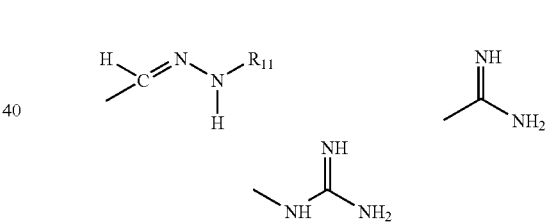

or by 1,3-dioxolane or 1,3-dioxane which is optionally mono- or polysubstituted, preferably mono-substituted, by methyl; or denote phenyl-$C_1$–$C_6$-alkylene, preferably phenyl-$C_1$–$C_4$-alkylene, phenyl-$C_2$–$C_6$-alkenylene or phenyl-$C_2$–$C_6$-alkynylene, in which the phenyl ring is optionally substituted, either directly or via a $C_1$–$C_4$-alkylene group, with one or more, preferably one, of the following groups, —$C_1$–$C_3$-alkyl, —CN, —$CH_2NR_6R_7$, —$NO_2$, —OH, —$OR_8$, —$CH_2$—NH—$SO_2$—$R_8$, —$NHCOR_8$, —$NHCONR_6R_7$, halogen, —$OCOR_8$, —$OCH_2COOH$, —$OCH_2COOR_8$, —$CH_2OCOR_8$, —$SO_2R_5$, —$OCH_2$—$CONR_6R_7$, —$OCH_2CH_2OH$, —$OCH_2$—$CH_2$—$NR_6R_7$, —$CONHSO_2R_8$, —$OCH_2CH_2OR_8$, —COOH, —$COOR_8$, —$CF_3$, cyclopropyl, —$CONR_6R_7$, —$CH_2OH$, —$CH_2OR_8$, —CHO, —$SR_8$, —$SOR_8$, —$SO_2R_8$, —$SO_3H$, —$PO_3H_2$, —$SO_2NR_6R_7$, —$OCH_2$—$CH_2OCOR_8$, —CH=NOH, —CH=$NOR_8$, —$COR_9$, —$CH(OH)R_9$, —$CH(OR_8)_2$, —$NHCOOR_8$, —$CH_2CONHSO_2R_8$, —CH=CH—$R_{10}$, —$OCONR_6R_7$, —$CH_2$—O—$CONR_6R_7$, —$CH_2$—$CH_2$—O—$CONR_6R_7$,

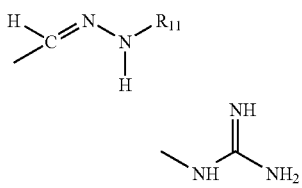

or by 1,3-dioxolane or 1,3-dioxane which is optionally mono- or polysubstituted, preferably monosubstituted, by methyl; or denote $C_3$–$C_7$-cycloalkyl-$C_1$–$C_6$-alkylene-, $C_3$–$C_7$-cycloalkyl-$C_2$–$C_6$-alkenylene-, $C_3$–$C_7$-cycloalkyl-$C_2$–$C_6$-alkynylene-, in which the cycloalkyl group may optionally be substituted, either directly or via a $C_{1-4}$-alkylene group, by —CN, —$CH_2NR_6R_7$, =O, —OH, —$OR_8$, —$NR_6R_7$, —$NHCOR_8$, —$NHCONR_6R_7$, halogen, —$OCOR_8$, —$OCH_2COOH$, —$OCH_2COOR_8$, —$CH_2OCOR_8$, —$SO_2R_5$, —$OCH_2CONR_6R_7$, —$OCH_2CH_2OH$, —$OCH_2$—$CH_2$—$NR_6R_7$, —$OCH_2CH_2OR_8$, —COOH, —$COOR_8$, —$CONR_6R_7$, —$CH_2OH$, —$CH_2OR_8$, —CHO, —$SR_8$, —$SOR_8$, —$SO_2R_8$, —$SO_3H$, —$PO_3H_2$, —$SO_2NR_6R_7$, —$OCH_2$—$CH_2$—$OCOR_8$, —CH=NOH, —CH=$NOR_8$, —$COR_9$, —CH(OH)$R_9$, —$CONHSO_2R_8$, —CH($OR_8$)$_2$, —$NHCOOR_8$, —CH=CH—$R_{10}$, —$OCONR_6R_7$, —$CH_2$—O—$CONR_6R$7, —$CH_2$—$CH_2$—O—$CONR_6R_7$,

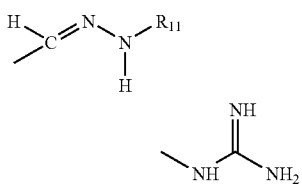

or by 1,3-dioxolane or 1,3-dioxane which is optionally mono- or polysubstituted, preferably monosubstituted, by methyl; or denote a group of the formula A—$C_1$–$C_6$-alkylene-, A—CONH—$C_1$–$C_6$-alkylene-, A—CONH—$C_2$–$C_6$-alkenylene-, A—CONH—$C_2$–$C_6$-alkynylene-, A—NH—CO—$C_1$–$C_6$-alkylene, A—NH—CO—$C_2$–$C_6$-alkenylene, A—NH—CO—$C_2$–$C_6$ alkynylene, A—$C_2$–$C_6$-alkenylene- or A—$C_2$–$C_6$-alkynylene, wherein A is a C- or N-linked 5- or 6-membered heterocyclic ring, 5- or 6-membered aromatic ring, or 5-or 6-membered heteroaromatic ring which contains nitrogen, oxygen or sulphur as heteroatoms and may optionally be mono- or polysubstituted, preferably monosubstituted, by $C_1$–$C_4$-alkyl, halogen, —$OR_8$, —CN, —$NO_2$, —$NH_2$, —$CH_2NR_6R_7$, —OH, =O, a ketal, —COOH, —$SO_3H$, —$PO_3H_2$, —$COOR_8$, —$CONR_6R_7$, —$COR_9$, —$SO_2$—$R_8$, —$CONR_6R_7$ or

$R_5$ denotes $C_1$–$C_4$-alkyl, optionally substituted by OH, $OCOR_8$, $NH_2$, $NR_6R_7$ or $NHCOR_8$, and $R_5$ preferably represents —$CH_2$—$CH_2$—OH, —$CH_2CH_2OCOR_8$, —$CH_2$—$CH_2$—$CH_2$—OH; —$CH_2$—$CH_2CH_2OCOR_8$;

$R_6$ denotes hydrogen, an optionally substituted $C_3$–$C_6$-cycloalkyl group, a branched or unbranched alkyl-, alkenyl- or alkynyl group having up to 10 carbon atoms, preferably a $C_1$–$C_8$-alkyl group, which may optionally be substituted by hydroxy, phenyl, substituted phenyl, amino, substituted amino, $C_1$ to $C_8$, preferably $C_1$ to $C_4$-alkoxy, or it denotes —(CH$_2$)$_m$—$NHCOOR_8$ wherein m=1, 2, 3 or 4;

$R_7$ denotes hydrogen, an optionally substituted $C_3$–$C_6$-cycloalkyl group, a branched or unbranched alkyl-, alkenyl- or alkynyl group having up to 10, preferably 1–4, carbon atoms, which may optionally be substituted by hydroxy, phenyl, substituted phenyl, amino, substituted amino, $C_1$ to $C_8$, preferably $C_1$ to $C_4$-alkoxy, or it denotes —(CH$_2$)$_m$—$NHCOOR_8$ wherein m=1, 2, 3 or 4; preferably hydrogen, or $R_6$ and $R_7$ together with the nitrogen atom form a saturated or unsaturated 5- or 6-membered ring which may contain as heteroatoms nitrogen, oxygen or sulphur, while the heterocyclic ring may be substituted by a branched or unbranched $C_1$- to $C_4$-alkyl group, preferably methyl, or may carry one of the following groups: —(CH$_2$)$_n$—$NH_2$, =O, a ketal- preferably —O—$CH_2$—$CH_2$—O—, —(CH$_2$)$_n$.NH—$C_1$–$C_4$-alkyl, —(CH$_2$)$_n$—N($C_1$–$C_8$-alkyl), —(CH$_2$)$_n$—NH-$COOR_8$, (n=2, 3, 4), halogen, —$OR_8$, —CN, —$NO_2$, —$NH_2$, —$CH_2NR_6R_7$, —OH, —COOH, —$SO_3H$, —$PO_3H_2$, —$COOR_8$, —$CONR_6R_7$, —$SO_2R_8$, $R_8$ denotes hydrogen, $C_1$–$C_8$-alkyl or $C_2$–$C_8$-alkenyl or $C_2$–$C_8$-alkynyl optionally substituted with $CO_2H$, a benzyl- or phenyl-group, which is optionally mono- or polysubstituted by $OCH_3$;

$R_9$ denotes $C_1$–$C_8$-alkyl or $C_2$–$C_8$-alkenyl or $C_2$–$C_8$-alkynyl optionally substituted with $CO_2H$, optionally substituted phenyl, optionally substituted benzyl, $C_3$–$C_6$-cycloalkyl, and $R_{10}$ denotes —$COOR_8$, —$CH_2OR_8$, —$CONR_6R_7$, hydrogen, $C_1$–$C_3$-alkyl, optionally substituted phenyl, —$CH_2NR_6R_7$.

Examples of 5- or 6-membered aromatic or heteroaromatic rings containing 0 to 4 heteroatoms selected from the group consisting of N, O and S include, but are not limited to those compounds shown in the Examples or named below.

Compounds as described above may be prepared in accordance with the techniques known in the art such as described in U.S. Pat. No. 5,719,279 to Kufner-Muhl et al., U.S. Pat. No. 5,786,360 to Neely, U.S. Pat. No. 6,489,332 to Neely, the techniques described in the Examples below, and variations of the foregoing that will be obvious to those skilled in the art of synthetic organic chemistry in light of the disclosure herein. Specific examples of compounds of the present invention that can be prepared by such techniques include but are not limited to:

3-[2-(4-acetaminophenyl)ethyl]-8-benzyl-1-butylxanthine;
3-[2-(2-acetaminophenyl)ethyl]-8-benzyl-1-pentylxanthine;
3-[2-(4-acetaminophenyl)ethyl]-8-benzyl-1-hexylxanthine;
3-[2-(4-acetaminophenyl)ethyl]-8-benzyl-1-propylxanthine;
3-[2-(4-acetaminophenyl)ethyl]-8-(3-chlorobenzyl)-1-propylxanthine;
3-[2-(3-acetaminophenyl)ethyl]-1-propyl-8-[(pyrimidin-5-yl)methyl]xanthine;
3-[2-(3-acetaminophenyl)ethyl]-8-[(1,3,4-oxadiazol-5-yl)methyl]-1-propylxanthine;
3-[2-(4-acetaminophenyl)ethyl]-1-propyl-8-(3-sulfonoxybenzyl)xanthine;
3-[2-(4-acetaminophenyl)ethyl]-1-propyl-8-(4-sulfonoxybenzyl)xanthine;
8-(3-aminobenzyl)-1-pentyl-3-(2-phenylethyl)xanthine;

8-(3-aminobenzyl)-3-(2-phenylethyl)-1-propylxanthine;
8-(2-aminobenzyl)-3-[2-(2-aminophenyl)ethyl]-1-propylxanthine;
8-(3-aminobenzyl)-3-[2-(3-aminophenyl)ethyl]-1-propylxanthine;
3-[2-[2-(6-aminohexanoyl)aminophenyl]ethyl]-8-benzyl-1-(3-methoxypropyl)xanthine;
3-[2-[3-(6-aminohexanoyl)aminophenyl]ethyl]-8-benzyl-1-(3-methoxypropyl)xanthine;
3-[2-[2-(6-aminohexanoyl)aminophenyl]ethyl]-8-benzyl-1-propylxanthine;
3-[2-[3-(6-aminohexanoyl)aminophenyl]ethyl]-8-benzyl-1-propylxanthine;
3-[2-(2-aminophenyl)ethyl]-8-benzyl-1-(3-dimethylaminopropyl)xanthine;
3-[2-(3-aminophenyl)ethyl]-8-benzyl-1-(3-dimethylaminopropyl)xanthine;
3-[2-(4-aminophenyl)ethyl]-8-benzyl-1-(8-sulfonoxyoctyl)xanthine;
3-[2-(4-aminophenyl)ethyl]-8-benzyl-1-(5-sulfonoxypentyl)xanthine;
3-[2-(2-aminophenyl)ethyl]-8-benzyl-1-(3-methoxypropyl)xanthine;
3-[2-(3-aminophenyl)ethyl]-8-benzyl-1-(3-methoxypropyl)xanthine;
3-[2-(2-aminophenyl)ethyl]-8-benzyl-1-(3-sulfonoxypropyl)xanthine;
3-[2-(3-aminophenyl)ethyl]-8-benzyl-1-(3-sulfonoxypropyl)xanthine;
3-[2-(4-aminophenyl)ethyl]-8-(4-fluorobenzyl-1-(3-sulfonoxypropyl)xanthine;
3-[2-(3-aminophenyl)ethyl]-1-butyl-8-[(pyridazin-4-yl)methyl]xanthine;
3-[2-(4-aminophenyl)ethyl]-1-butyl-8-[(pyridazin-4-yl)methyl]xanthine;
3-[2-(4-amino-3-chlorophenyl)ethyl]-1-propyl-8-[(pyridazin-4-yl)methyl]xanthine;
3-[2-(4-amino-2-chlorophenyl)ethyl]-1-propyl-8-[(1H-pyrrol-3-yl)methyl]xanthine;
3-[2-(4-amino-2-fluorophenyl)ethyl]-1-propyl-8-[(1H-pyrrol-3-yl)methyl]xanthine;
3-[2-(4-aminophenyl)ethyl]-1-propyl-8-[(1H-1,3,4-triazol-5-yl)methyl]xanthine;
3-[2-(2-aminophenyl)ethyl]-1-propyl-8-[(1H-1,2,4-triazol-5-yl)methyl]xanthine;
3-[2-(3-aminophenyl)ethyl]-8-[(1,2,4-oxadiazol-5-yl)methyl]-1-propylxanthine;
3-[2-(4-aminophenyl)ethyl]-1-propyl-8-[(4-pyridyl)methyl]xanthine N-oxide;
3-[2-(4-aminophenyl)ethyl]-1-propyl-8-[(oxazol-2-yl)methyl]xanthine;
3-[2-(2-aminophenyl)ethyl]-8-[(isoxazol-4-yl)methyl]-1-propylxanthine;
3-[2-(2-aminophenyl)ethyl]-8-[(5-chloroisoxazol-4-yl)methyl]-1-propylxanthine;
3-[2-(4-aminophenyl)ethyl]-8-(2,4-difluorobenzyl)-1-propylxanthine;
3-[2-(2-aminophenyl)ethyl]-8-[(5-fluoroisoxazol-4-yl)methyl]-1-pentylxanthine;
3-[2-(4-aminophenyl)ethyl]-8-[(4-fluoro-2-oxazolyl)methyl]-1-propylxanthine;
3-[2-(4-aminophenyl)ethyl]-8-[(5-fluoro-2-oxazolyl)methyl]-1-propylxanthine;
3-[2-(4-aminophenyl)ethyl]-8-[(isothiazol-3-yl)methyl]-1-propyl-xanthine;
3-[2-(3-aminophenyl)ethyl]-1-propyl-8-[(pyrimidin-2-yl)methyl]xanthine;
3-[2-(2-aminophenyl)ethyl]-8-[(4-fluoro-3-isothiazolyl)methyl]-1-propylxanthine;
3-[2-(4-aminophenyl)ethyl]-8-[(5-fluoropyrimidin-2-yl)methyl]-1-propylxanthine;
3-[2-(3-aminophenyl)ethyl]-8-[(1,3,4-oxadiazol-5-yl)methyl]-1-pentylxanthine;
3-[2-(4-aminophenyl)ethyl]-1-propyl-8-[(1H-pyrazol-3-yl)methyl]xanthine;
3-[2-(3-aminophenyl)ethyl]-1-propyl-8-[(1H-pyrazol-3-yl)methyl]xanthine;
3-[2-(4-aminophenyl)ethyl]-1-pentyl-8-[(1H-pyrazol-3-yl)methyl]xanthine;
3-[2-(2-aminophenyl)ethyl]-1-propyl-8-[(pyrazin-2-yl)methyl]xanthine;
3-[2-(2-aminophenyl)ethyl]-1-butyl-8-[(3-fluoropyrazin-2-yl)methyl]xanthine;
3-[2-(2-aminophenyl)ethyl]-8-[(3-fluoropyrazin-2-yl)methyl]-1-pentylxanthine;
3-[2-(2-aminophenyl)ethyl]-8-[(3-fluoropyrazin-2-yl)methyl]-1-propylxanthine;
3-[2-(4-aminophenyl)ethyl]-1-pentyl-8-[(2-fluoro-1H-pyrazol-3-yl)methyl]xanthine;
3-[2-(4-aminophenyl)ethyl]-1-propyl-8-[(1H-pyrrol-3-yl)methyl]xanthine;
3-[2-(2-aminophenyl)ethyl]-1-propyl-8-[(pyridazin-4-yl)methyl]xanthine;
3-[2-(4-aminophenyl)ethyl]-1-propyl-8-[(1H-tetrazol-1-yl)methyl]xanthine;
3-[2-(2-aminophenyl)ethyl]-1-propyl-8-[(1H-tetrazol-5-yl)methyl]xanthine;
3-[2-(3-aminophenyl)ethyl]-1-propyl-8-[(furan-3-yl)methyl]xanthine;
3-[2-(4-aminophenyl)ethyl]-1-propyl-8-[(furan-2-yl)methyl]xanthine;
3-[2-(4-aminophenyl)ethyl]-1-propyl-8-[(thiophen-3-yl)methyl]xanthine;
3-[2-(4-aminophenyl)ethyl]-1-propyl-8-(3-sulfonoxybenzyl)xanthine;
8-benzyl-3-[2-(3-aminophenyl)ethyl]-1-propylxanthine;
8-benzyl-3-[2-(3-aminophenyl)ethyl]-1-butylxanthine;
8-benzyl-3-[2-(4-aminophenyl)ethyl]-1-propylxanthine;
8-benzyl-3-[2-(4-carboxyphenyl)ethyl]-1-propylxanthine;
8-benzyl-3-[2-(3-chlorophenyl)ethyl]-1-propylxanthine;
8-benzyl-3-[2-(2,4-difluorophenyl)ethyl]-1-pentylxanthine;
8-benzyl-3-[2-(2,4-difluorophenyl)ethyl]-1-propylxanthine;
8-benzyl-3-[2-(3-nitrophenyl)ethyl]-1-propylxanthine;
8-benzyl-3-[2-(isothiazol-3-yl)ethyl]-1-propylxanthine;
8-benzyl-3-[2-(thiazol-3-yl)ethyl]-1-propylxanthine;
8-benzyl-3-[2-(isoxazol-3-yl)ethyl]-1-propylxanthine;
8-benzyl-3-[2-(1,3,4-oxadiazol-5-yl)ethyl]-1-pentylxanthine;
8-benzyl-3-[2-(1,2,4-oxadiazol-5-yl)ethyl]-1-propylxanthine;
8-benzyl-3-[2-(4-fluorophenyl)ethyl]-1-pentylxanthine;
8-benzyl-3-[2-(4-nitrophenyl)ethyl]-1-propylxanthine;
8-benzyl-3-[2-phenylethyl]-1-pentylxanthine;
8-benzyl-3-[2-phenylethyl]-1-propylxanthine;
8-benzyl-1-propyl-3-[4-(2-sulfonoxyphenyl)butyl]xanthine;
8-benzyl-1-propyl-3-[4-(3-sulfonoxyphenyl)butyl]xanthine;
8-benzyl-1-propyl-3-[2-(2-sulfonoxyphenyl)ethyl]xanthine;
8-benzyl-1-propyl-3-[2-(3-sulfonoxyphenyl)ethyl]xanthine;
3-[2-(4-bromophenyl)ethyl]-1-propyl-8-[(4-pyridyl)methyl]xanthine;
3-[2-(2-carboxyphenyl)ethyl]-8-(3-fluorobenzyl)-1-propylxanthine;
3-[2-(2-carboxyphenyl)ethyl]-8-(3-nitrobenzyl)-1-propylxanthine;

3-[2-(2-carboxyphenyl)ethyl]-1-propyl-8-[(2-pyridyl)methyl]xanthine;

3-[2-(2-carboxyphenyl)ethyl]-1-propyl-8-[(2-pyridyl)methyl]xanthine;

3-[2-(4-chlorophenyl)ethyl]-1-propyl-8-[(4-pyridyl)methyl]xanthine N-oxide;

3-[2-(2,4-diaminophenyl)ethyl]-8-[(5-fluoro-2-oxazolyl)methyl]-1-propylxanthine;

3-[2-(2,4-difluorophenyl)ethyl]-1-propyl-8-[(2-pyridyl)methyl]xanthine N-oxide;

3-[2-(4-fluorophenyl)ethyl]-1-propyl-8-[(2-pyridyl)methyl]xanthine N-oxide;

3-[2-(2-fluorophenyl)ethyl]-1-propyl-8-[(pyrazin-2-yl)methyl]xanthine;

3-[2-(3-fluorophenyl)ethyl]-8-[(1,3,4-oxadiazol-5-yl)methyl]-1-propylxanthine;

3-[2-(4-nitrophenyl)ethyl]-1-propyl-8-[(1H-pyrazol-3-yl)methyl]xanthine;

3-[2-(3-nitrophenyl)ethyl]-8-[(1,3,4-oxadiazol-5-yl)methyl]-1-propylxanthine;

3-[2-(2-nitrophenyl)ethyl]-1-propyl-8-[(1H-1,2,4-triazol-5-yl)methyl]xanthine;

3-[2-(2-nitrophenyl)ethyl]-8-[(4-fluoro-3-isothiazolyl)methyl]-1-propylxanthine;

3-[2-(3-nitrophenyl)ethyl]-1-propyl-8-[(pyridazin-4-yl)methyl]xanthine;

3-[2-(3-nitrophenyl)ethyl]-8-[(1,2,4-oxadiazol-5-yl)methyl]-1-propylxanthine;

3-(2-phenyl)ethyl-8-benzyl-1-(8-sulfonoxyoctyl)xanthine;

3-(2-phenyl)ethyl-8-benzyl-1-(5-sulfonoxypentyl)xanthine;

3-(2-phenylethyl)-1-propyl-8-[(2-fluoro-2-pyridyl)methyl]xanthine N-oxide;

3-(2-phenylethyl)-1-propyl-8-[(1,2,4-oxadiazol-3-yl)benzyl]xanthine;

3-(2-phenylethyl)-1-propyl-8-[(1,3,4-oxadiazol-5-yl)benzyl]xanthine;

3-(2-phenylethyl)-1-propyl-8-[(1H-pyrazol-3-yl)benzyl]xanthine;

3-(2-phenylethyl)-1-propyl-8-[(2-pyridyl)methyl]xanthine;

3-(2-phenylethyl)-1-propyl-8-[(3-pyridyl)methyl]xanthine;

3-(2-phenylethyl)-1-propyl-8-[(4-pyridyl)methyl]xanthine;

3-(2-phenylethyl)-1-propyl-8-[(2-pyridyl)methyl]xanthine N-oxide;

3-(2-phenylethyl)-1-propyl-8-[(3-pyridyl)methyl]xanthine N-oxide;

3-(2-phenylethyl)-1-propyl-8-[(4-pyridyl)methyl]xanthine N-oxide;

3-(2-phenylethyl)-1-propyl-8-(3-sulfonoxybenzyl)xanthine;

3-(2-phenylethyl)-1-propyl-8-(4-sulfonoxybenzyl)xanthine;

and pharmaceutically acceptable salts, hydrates and prodrugs thereof.

The compound of the present invention may form pharmaceutically acceptable salts with both organic and inorganic acid and bases. Examples of suitable acids for salt formation are hydrochloric, sulfuric, phosphoric, acetic, citric, oxalic, malonic, salicylic, ascorbic, maleic, methanesulfonic, benzenesulfonic, p-toluenesulfonic and the like. Any of the amine acid addition salts may also be used. The salts are prepared by contacting the free base form of the compound with an appropriate amount of the desired acid in a manner known to one skilled in the art. Examples of suitable bases for salt formation are sodium hydroxide, sodium carbonate, sodium bicarbonate, potassium hydroxide, calcium hydroxide, ammonia, organic amines, and the like. The salts may be prepared by contacting the free acid form of the compound with an appropriate amount of the desired base in a manner known to one skilled in the art.

Active compounds of the invention may be provided in the form of prodrugs. The term "prodrug" refers to compounds that are transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

The invention also provides $A_1$ adenosine receptor antagonist compounds with radioactive or non-radioactive labels. Such labelled compounds are useful as assay-type probes or conjugates, and may be used to obtain quantitative binding measurements of the $A_1$ adenosine receptor antagonist compounds. For the purposes of the invention, "assay-type probes" refers to those materials which are useful for enhancing the selectivity of the quantitative analysis of the $A_1$ adenosine receptor compounds of the invention. Examples of such assay-type probes are described in U.S. Pat. No. 5,248,770 to Jacobson et al., the disclosure of which is incorporated herein by reference in its entirety. The probes are highly useful in that they have little adverse effect on the affinity of the compounds of the present invention. Radioactive markers include, but are not limited to, an electric spin marker, a $^{19}F$ NMR probe, a radioactive $^{18}F$ isotope marker, a radioactive iodine marker (e.g., $^{125}I$), a radioactive $^3H$ marker, tritium, and a complex of a metal atom or a metal ion and a chelating agent. An exemplary metal ion is a radioactive isotope of technetium or indium. An exemplary chelating agent is diethylene pentacetic anhydride.

Various non-radioactive materials may be used in labelling the present $A_1$ adenosine receptor compounds. Numerous examples are presented in U.S. Pat. No. 5,248,770 to Jacobson et al. Biotin is used as a common non-radioactive label for such probes, as described in R. W. Old et al. *Principals of Gene Manipulation*, 4th ed: 328–331 (1989). To facilitate labelling the compounds with biotin or any other appropriate material, a spacer component may be added to the compound according to an accepted method. Such a method is described in the Jacobson et al. '770 patent. Exemplary spacer components include, but are not limited to, an oligopeptide, triglycidyl, and N-hydroxysuccinimide ester.

Biotin may be bonded to any suitable linkage provided by substituents on the compound structure in accordance with any accepted and suitable technique. For example, referring to compound (I) as defined herein, biotin may be bonded to the hydroxy group on $R_6$ when the compound contains $(CH_2)_mOH$ at $R_6$ with m defined herein; to the amino group present on either of $R_7$ or $R_8$ when $NH_2$ is contained at these positions; or to the carboxyl group present when $R_7$ and $R_8$ are $R_9COOH$ or $R_{10}COOH$ respectively, with $R_9$ and $R_{10}$ defined herein. Additionally, the biotin may be bonded to a hydroxyl group present on $R_8$, when $R_8$ is $(CH_2)_sOH$ with s being defined herein. Biotin may also be bonded to $R_7$, when $R_7$ is $(CH_2)_tOH$ with t being defined herein. The biotin-labeled probes may be detected through appropriate and known analytical techniques.

Fluorescent dyes may also be employed as a non-radioactive labels and are applied to appropriate locations on the compounds of the invention. Such dyes include, but are not limited to, tetramethylrhodamine, fluorescein isothiocyanate, and mixtures thereof. Other non-radioactive materials include for example, nitrobenzoxadiazole; 2,2,6,6-tetramethyl-piperindinyloxy-4-isothiocyanate; and mixtures thereof.

The invention is also directed to a pharmaceutical composition which includes the compound of the present invention and a pharmaceutically acceptable carrier.

The pharmaceutical composition is particularly useful in applications relating to organ preservation in vivo or in situ, perfusion of an isolated organ either removed or contained within the body (e.g., when an organ is transported for transplantation), cardiopulmonary bypass, perfusion of an extremity or limb, and the like. The compounds may be used in intra-articular, intra-thecal, gastrointestinal, and genital urinary applications, as well as in any cavity or lumen such as, for example, the thoracic cavity or ear canal.

The pharmaceutical composition may be employed, as an example, in oral dosage form as a liquid composition. Such liquid compositions can include suspension compositions or syrup compositions and can be prepared with such carriers as water; a saccharide such as sucrose, sorbitol, fructose, and the like; a glycol such as polyethyleneglycol, polypropyleneglycol, and the like; an oil such as sesame oil, olive oil, soybean oil, and the like; an antiseptic such as p-hydroxybenzoic acid esters and the like; and a flavor component such as a fruit flavor or a mint flavor. The pharmaceutical composition may also be in the form of powder, pills, capsules, and tablets and can be prepared with various carriers. Suitable carriers include, but are not limited to, lactose, glucose, sucrose, mannitol, and the like; disintegrators such as starch, sodium alginate, and the like; binders such as polyvinyl alcohol, hydroxypropyl cellulose, gelatin, and the like; surfactants such as, for example, fatty acid esters; and plasticizers such as, for example, glycerins. The composition of the present invention is especially useful when applied sublingually. It should be noted that in the preparation of the tablets and capsules, a solid pharmaceutical carrier is used. Advantageously, the pharmaceutical composition may be used in the form of, for example, eye drops or an aerosol.

Other types of pharmaceutical compositions may be employed in the form of a suppository, a nasal spray, and an injectable solution. These compositions are prepared using appropriate aqueous solutions which may include, but are not limited to, distilled water, and saline and buffer additives. Other components may be employed such as organic materials including neutral fatty bases. Additionally, the pharmaceutical composition may be utilized in a transdermal application.

Biopolymers may be used as carriers in the above pharmaceutical compositions. Exemplary biopolymers may include, for example, proteins, sugars, lipids or glycolipids. See, e.g., C. Wilson, PCT Application WO 02/095391 (Published Nov. 22, 2002).

The $A_1$ receptor antagonists of the present invention are particularly useful as, for example, anti-allergenics, anti-inflammatory agents, CNS stimulants, diuretics, anti-asthmatics, cardiotonics, coronary vasodilators, and anti-tussives and as agents for the treatment of viral or retroviral infections and immune deficiency disorders such as acquired immunodefiency syndrome (AIDS).

The present invention also provides a method of treating A1 adenosine receptor related disorders, such disorders including but not limited to congestive heart failure, hypertension, such as systemic hypertension and pulmonary hypertension, ischemia-reperfusion organ injury, endotoxin-related tissue injury, renal failure, Alzheimer's disease, depression, obesity, asthma, diabetes, cystic fibrosis, allergic conditions, including, but not limited to allergic rhinitis and anaphylactic shock, autoimmune disorders, inflammatory disorders, chronic obstructive pulmonary disorders, chronic cough, coronary artery disease, biliary colic, postoperative ileus, fibrosis, sclerosis, Adult Respiratory Distress Syndrome (ARDS), Acute Lung Injury (ALI), Severe Acute Respiratory Syndrome (SARS), septicemia, substance abuse, drug dependence, and Parkinson's disease.

The dosage of the active agent will depend upon the condition being treated, the age and condition of the subject, the route of administration, etc. In general the dosage can be determined in accordance with known techniques. In one embodiment the dosage of the active agent may, for example, be from 1 or 10 to 300 or 800 mg per adult subject.

Combination treatments. The compounds described herein may be used alone or in combination with other compounds for the treatment of the disorders described herein, including but not limited to those compounds described in C. Wilson, PCT Application WO 03/103675, published Dec. 18, 2003.

Thus, according to other embodiments of the invention, the present invention relates to a method of treating $A_1$ adenosine receptor-related disorders, comprising concurrently administering:

(a) an $A_1$ adenosine receptor antagonist as described above, or a pharmaceutically acceptable salt thereof; with (b) an additional active agent such as a compound selected from the group consisting of fluticasone propionate, salmeterol, theophylline, $A_1$ adenosine receptor antagonists, $A_{2a}$ adenosine receptor agonists, $A_{2b}$ adenosine receptor antagonists, $A_3$ adenosine receptor antagonists, $P_{2y}$ purinoceptor agonists, and $P_{2x}$ purinoceptor antagonists, and combinations thereof, in an amount effective to treat the $A_1$ adenosine receptor-related disorder.

According to still other embodiments of the present invention, the present invention relates to a method of treating $A_1$ adenosine receptor-related disorders, comprising concurrently administering an $A_1$ adenosine receptor antagonist as described above with at least one additional active agent such as described above effective to treat $A_1$ adenosine receptor-related disorders, wherein the $A_1$ adenosine receptor-related disorder is as described above.

Administration of compounds in combination may be carried out in like manner as described above, with the active compound and the additional active agent being administered in the same or different carrier. Pharmaceutical formulations containing such combinations of active agents may also be prepared in like manner as described above.

The present invention is explained in greater detail in the following non-limiting Examples.

EXAMPLE 1

Synthesis of 5,6-Diamino-1-[2-(4-nitrophenyl)ethyl]-3-propyluracil (6)

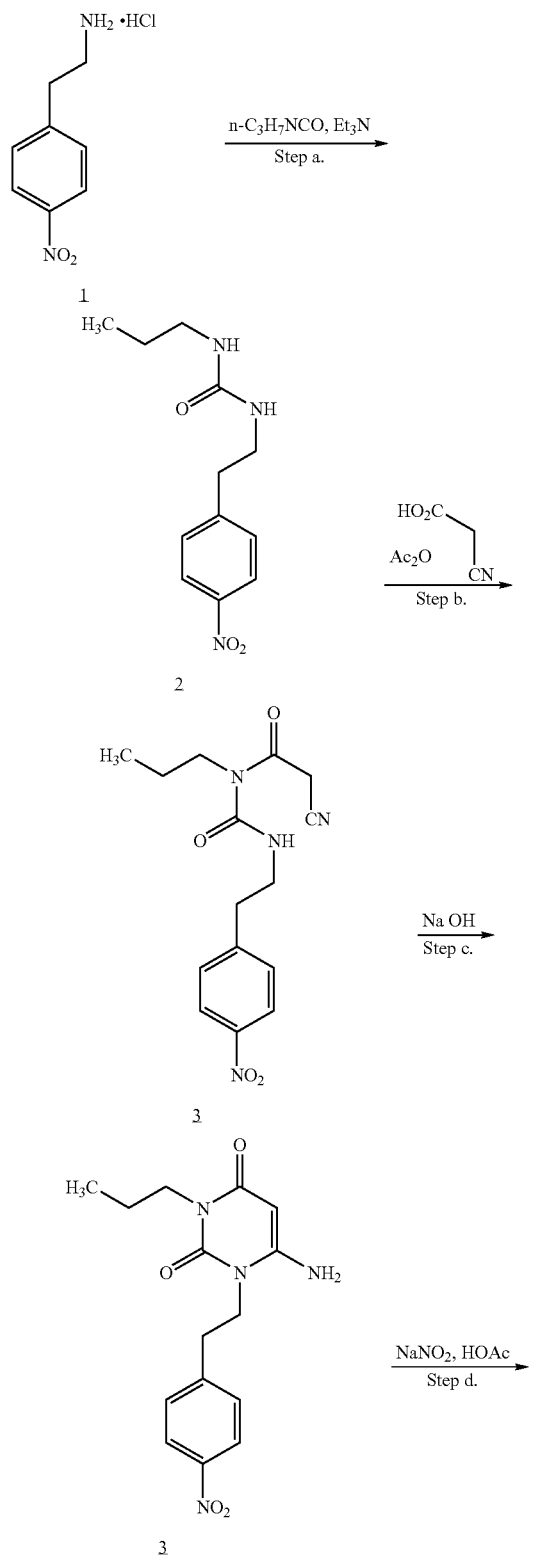

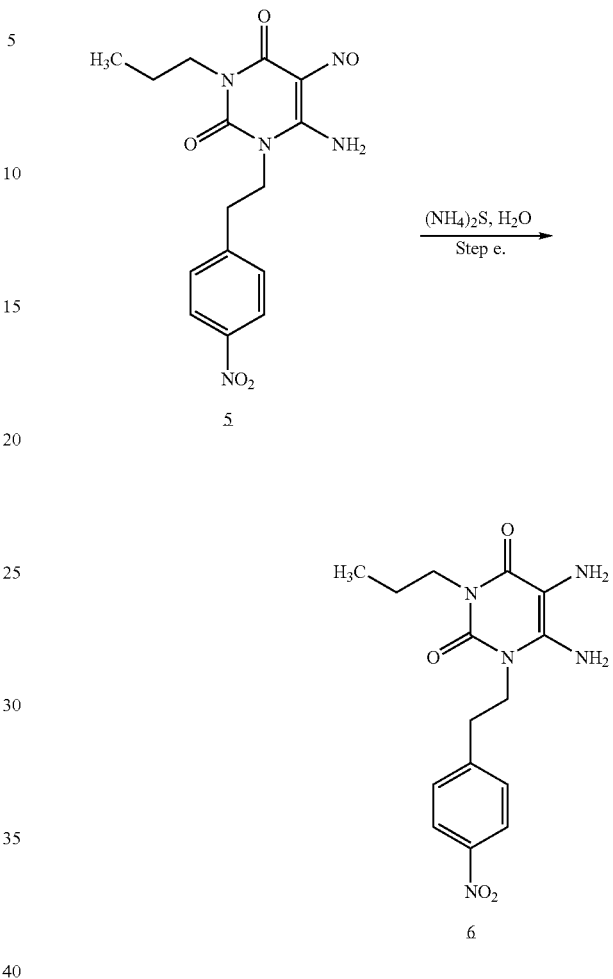

Step a: Conversion of 4-Nitrophenethylamine Hydrochloride (1) to 1-[2-(4-Nitrophenyl)ethyl]-1'-propylurea (2). To a slurry of 777 gm of 4-nitrophenethylamine hydrochloride (1) and 11.2 L of toluene was added slowly, 620 mL of triethylamine and this mixture was stirred for 30 min. at room temperature. To this suspension was then added slowly, 398 mL of n-propyl isocyanate, and the mixture was stirred overnight at room temperature to give a solid precipitate. The heterogeneous mixture was filtered and the isolated solids were washed with 1.5 L of toluene and then air dried. The 2.3 kg of crude product was stirred with 6 L of water to dissolve residual triethylamine hydrochloride. The solids were isolated by filtration and air dried. This material was dissolved in 4 L of absolute ethanol and 1 L of water was added to induce crystallization. The solids were filtered, washed with 2 L of 1:1 ethanol-water and air dried to yield a first crop of 880 gm of 1-[2-(4-nitrophenyl)ethyl]-1'-propylurea (2). The recrystallization mother liquors yielded an additional 39.8 gm of 1-[2-(4-nitrophenyl)ethyl]-1'-propylurea (2).

Step b: Conversion of 1-[2-(4-Nitrophenyl)ethyl]-1'-propylurea (2) to 1'-Cyanoacetyl-1-[2-(4-nitrophenyl)ethyl]-1'-propylurea (3). A thick mixture of 920 gm of 1-[2-(4-nitrophenyl)ethyl]-1'-propylurea (2) and 1.0 L of acetic anhydride was stirred and warmed to ca. 50 degrees C. To this mixture was added 343.2 gm of cyanoacetic acid and 0.5 L of acetic anhydride and this homogeneous mixture was stirred at 80–85 degrees C. for three hours. The mixture was cooled and concentrated under vacuum to remove acetic acid and residual acetic anhydride. The residue was triturated successively with 1.0 L portions of water, acetonitrile, toluene and ethyl acetate. The residue was then dried under vacuum to yield 1261 gm of a 2:1 mixture of 1'-cyanoacetyl-1-[2-(4-nitrophenyl)ethyl]-1'-propylurea (3) and its undesired isomer 1-cyanoacetyl-1-[2-(4-nitrophenyl)ethyl]-1'-propylurea. This material was dissolved in 2.2 L of hot ethyl acetate to which ca. 750 mL of hexanes were added to the cloud point and the mixture was allowed to cool to room temperature to induce crystallization. Filtration of the solid and air drying yielded 363 gm of 1'-cyanoacetyl-1-[2-(4-nitrophenyl)ethyl]-1'-propylurea (3). If needed, additional recrystallizations from ethyl acetate-hexanes could be carried out to provide pure 1'-cyanoacetyl-1-[2-(4-nitrophenyl)ethyl]-1'-propylurea (3).

Step c: Conversion of 1'-Cyanoacetyl-1-[2-(4-nitrophenyl)ethyl]-1'-propylurea (3) to 6-Amino-1-[2-(4-nitrophenyl)ethyl]-3-propyluracil (4). A mixture of ca. 2N sodium hydroxide was produced by dissolving 336 gm of solid sodium hydroxide in 4.2 L of water. To this warm solution was added, in portions, 312 gm of 1'-cyanoacetyl-1-[2-(4-nitrophenyl)ethyl]-1'-propylurea (3) and the mixture was stirred for 1 hour at 80 degrees C., then was cooled to room temperature with stirring to induce crystallization. The solids were isolated by filtration, washed with four 500 mL portions of water and vacuum dried at 65 degrees C. to yield 232 gm of crude 6-amino-1-[2-(4-nitrophenyl)ethyl]-3-propyluracil (4).

Step d: Conversion of 6-Amino-1-[2-(4-nitrophenyl)ethyl]-3-propyluracil (4) to 6-Amino-5-nitroso-1-[2-(4-nitrophenyl)ethyl]-3-propyluracil (5). To a solution of 232 gm of crude 6-amino-1-[2-(4-nitrophenyl)ethyl]-3-propyluracil (4), 4.0 L of water and ca. 2.0 L of ethanol at 80 degrees C. was added 55.3 gm of sodium nitrite in one portion, followed by the dropwise addition of 100 mL of glacial acetic acid. After stirring at 80 degrees C. for 20 minutes the mixture was allowed to cool to near room temperature, then was chilled in an ice bath to effect crystallization. The solids were isolated by filtration, washed with two 1.0 L portions of water and dried under vacuum to yield 244 gm of purple colored 6-amino-5-nitroso-1-[2-(4-nitrophenyl)ethyl]-3-propyluracil (5).

Step e: Conversion of 6-Amino-5-nitroso-1-[2-(4-nitrophenyl)ethyl]-3-propyluracil (5) to 5,6-Diamino-1-[2-(4-nitrophenyl)ethyl]-3-propyluracil (6). A mixture of 243 gm of 6-amino-5-nitroso-1-[2-(4-nitrophenyl)ethyl]-3-propyluracil (5), and 2.1 L of water was heated to reflux and 528 mL of a 50% aqueous solution of ammonium sulfide was added with stirring to control foaming. The dark solution was stirred at 90–100 degrees C. for 30 min. and allowed to cool with stirring for 1.5 hours. The mixture was then chilled in an ice bath to fully effect crystallization. The solids were isolated by filtration, washed with three 500 mL portions of water and dried under vacuum to yield 219 gm of a dark solid. This material was recrystallized from 1.0 L of acetonitrile to yield two crops totaling 169.5 gm of 5,6-diamino-1-[2-(4-nitrophenyl)ethyl]-3-propyluracil (6).

EXAMPLE 2

Synthesis of 8-Benzyl-3-[2-(4-nitrophenyl)ethyl]-1-propylxanthine (9)

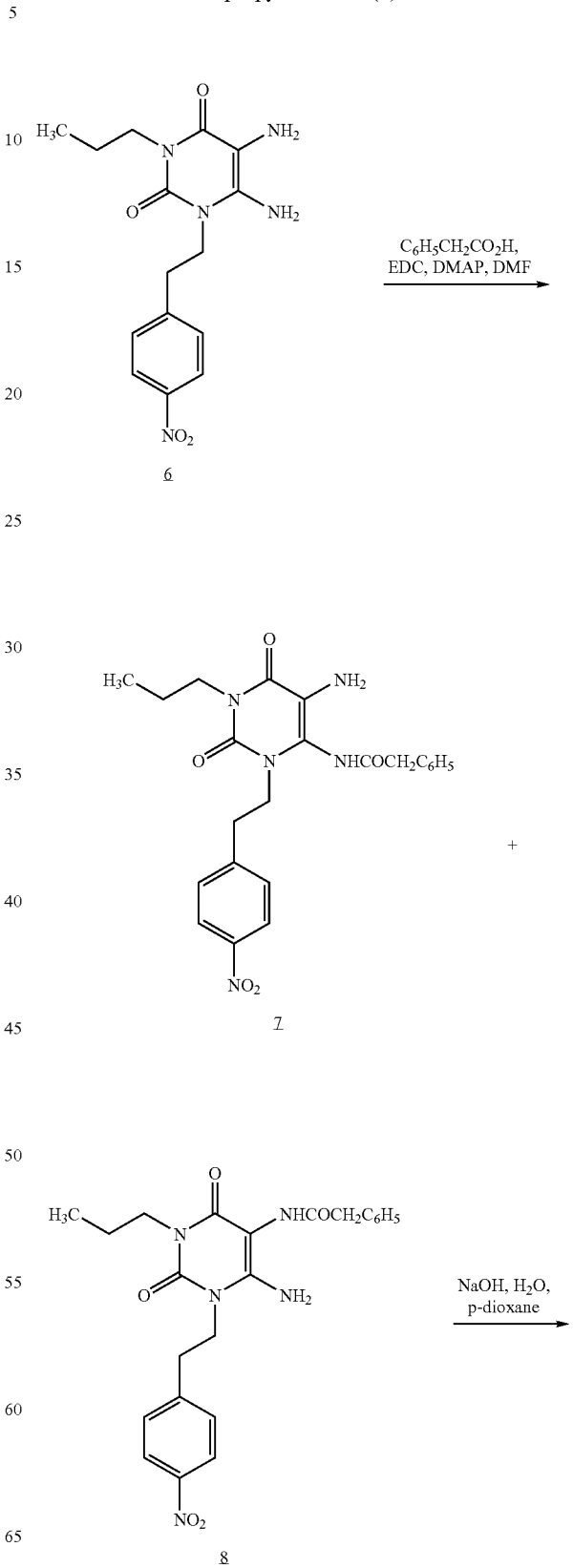

-continued

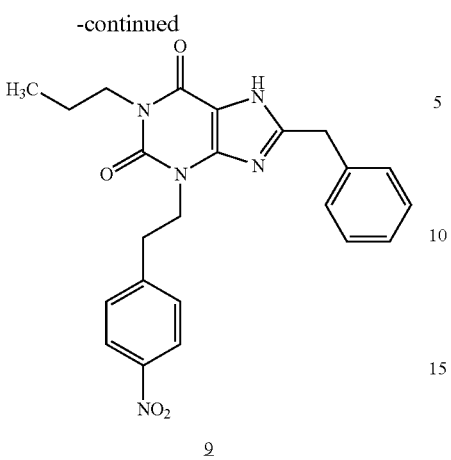

9

A solution of 44.9 gm of phenylacetic acid in 630 mL of dimethylformamide (DMF) was chilled in an ice water bath and 63.38 gm of 1-(3-dimethylaminopropyl)-3-ethylcarbodiimide hydrochloride (EDC) was added followed by 5.24 gm of 4-dimethylaminopyridine (DMAP). This mixture was stirred at ca. 4 degrees C. for 30 minutes and 100 gm of 5,6-diamino-1-[2-(4-nitrophenyl)ethyl]-3-propyluracil (6) was added in one portion. This mixture was stirred for 60 hr at room temperature. The dark homogeneous solution was poured into 700 mL of ice water with stirring to effect precipitation. The solids were isolated by filtration, washed with three 100 mL portions of water and dried under vacuum to yield 103 gm of a mixture of 5-amino-1-[2-(4-nitrophenyl)ethyl]-6-phenacetoamino-3-propyluracil (7) and 6-amino-1-[2-(4-nitrophenyl)ethyl]-5-phenacetoamino-3-propyluracil (8) intermediates. These solids were dissolved in 450 mL of p-dioxane, 600 mL of 2N aqueous sodium hydroxide was added and the mixture was heated at reflux for one hr. The solution was then chilled in an ice water bath and the pH adjusted to pH 4 with ca. 100 nL of concentrated hydrochloric acid to yield a precipitate. The solids were isolated by filtration, washed with three 100 mL portions of water and dried under vacuum to yield 82 gm of an orange solid. Recrystallization from hot ethyl acetate afforded 58.0 gm of 8-benzyl-3-[2-(4-nitrophenyl)ethyl]-1-propylxanthine (9).

EXAMPLE 3

Synthesis of 3-[2-(4-Aminophenyl)ethyl]-8-benzyl-1-propylxanthine

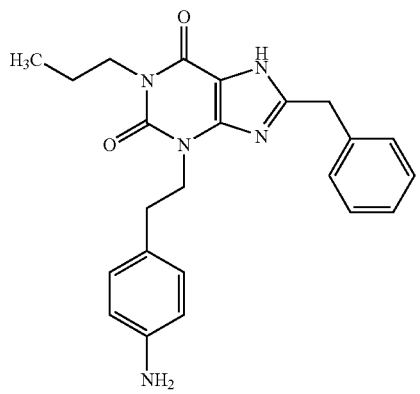

By methods well known in the art, 8-benzyl-3-[2-(4-nitrophenyl)ethyl]-1-propylxanthine (9) is reduced with hydrazine hydrate or hydrogen gas in the presence of a palladium catalyst to yield 3-[2-(4-aminophenyl)ethyl]-8-benzyl-1-propylxanthine.

EXAMPLE 4

Synthesis of 3-[2-(4-Aminophenyl)ethyl]-8-(4-fluorobenzyl)-1-propylxanthine

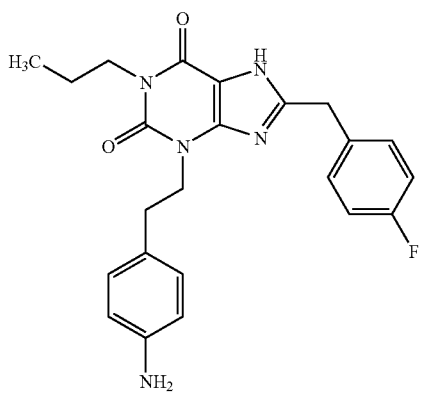

By the method of Example 2, 4-fluorophenylacetic acid is reacted with 5,6-diamino-1-[2-(4-nitrophenyl)ethyl]-3-propyluracil (6) to yield 8-(4-fluorobenzyl)-3-[2-(4-nitrophenyl)ethyl]-1-propylxanthine. By methods well known in the art, 8-(4-fluorobenzyl)-3-[2-(4-nitrophenyl)ethyl]-1-propylxanthine is reduced with hydrazine hydrate or hydrogen gas in the presence of a palladium catalyst to yield 3-[2-(4-aminophenyl)ethyl]-8-(4-fluorobenzyl)-1-propylxanthine.

EXAMPLE 5

Synthesis of 3-[2-(4-Aminophenyl)ethyl]-1-propyl-8-[(3-pyridyl)methyl]xanthine

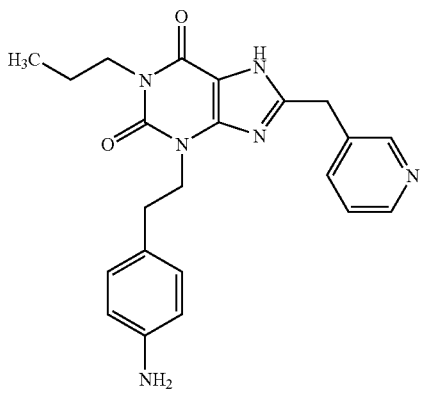

By the method of Example 2, 3-pyridylacetic acid is reacted with 5,6-diamino-1-[2-(4-nitrophenyl)ethyl]-3-propyluracil (6) to yield 3-[2-(4-nitrophenyl)ethyl]-1-propyl-8-[(3-pyridyl)methyl]xanthine. By methods well known in the art, 3-[2-(4-nitrophenyl)ethyl]-1-propyl-8-[(3-pyridyl)methyl]xanthine is reduced with hydrazine hydrate or hydrogen gas in the presence of a palladium catalyst to yield 3-[2-(4-aminophenyl)ethyl]-1-propyl-8-[(3-pyridyl)methyl]xanthine.

EXAMPLE 6

Synthesis of 3-[2-(4-Aminophenyl)ethyl]-1-propyl-8-[(thiophen-2-yl)methyl]xanthine

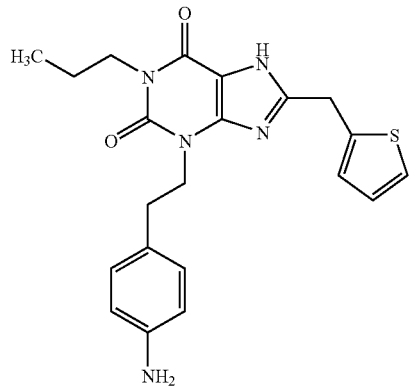

By the method of Example 2, 2-thiopheneacetic acid is reacted with 5,6-diamino-1-[2-(4-nitrophenyl)ethyl]-3-propyluracil (6) to yield 3-[2-(4-nitrophenyl)ethyl]-1-propyl-8-[(thiophen-2-yl)methyl]xanthine. By methods well known in the art, 3-[2-(4-nitrophenyl)ethyl]-1-propyl-8-[(thiophen-2-yl)methyl]xanthine is reduced with hydrazine hydrate or hydrogen gas in the presence of a palladium catalyst to yield 3-[2-(4-aminophenyl)ethyl]-1-propyl-8-[(thiophen-2-yl)methyl]xanthine.

EXAMPLE 7

Synthesis of 3-[2-(4-Aminophenyl)ethyl]-1-propyl-8-[(4-thiazolyl)methyl]xanthine

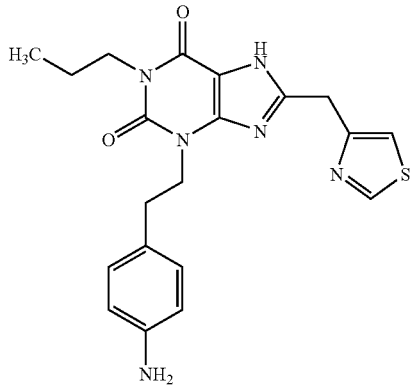

By the method of Example 2, 4-thiazolylacetic acid is reacted with 5,6-diamino-1-[2-(4-nitrophenyl)ethyl]-3-propyluracil (6) to yield 3-[2-(4-nitrophenyl)ethyl]-1-propyl-8-[(4-thiazolyl)methyl]xanthine. By methods well known in the art, 3-[2-(4-nitrophenyl)ethyl]-1-propyl-8-[(4-thiazolyl)methyl]xanthine is reduced with hydrazine hydrate or hydrogen gas in the presence of a palladium catalyst to yield 3-[2-(4-aminophenyl)ethyl]-1-propyl-8-[(4-thiazolyl)methyl]xanthine.

EXAMPLE 8

Synthesis of 3-[2-(4-Aminophenyl)ethyl]-1-propyl-8-[(1H-tetrazol-5-yl)methyl]xanthine

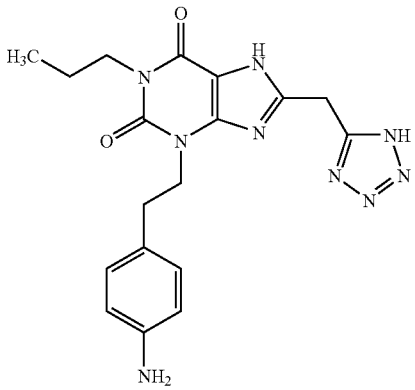

By the method of Example 2, 1H-tetrazole-5-acetic acid is reacted with 5,6-diamino-1-[2-(4-nitrophenyl)ethyl]-3-propyluracil (6) to yield 3-[2-(4-nitrophenyl)ethyl]-1-propyl-8-[(1H-tetrazol-5-yl)methyl]xanthine. By methods well known in the art, 3-[2-(4-nitrophenyl)ethyl]-1-propyl-8-[(1H-tetrazol-5-yl)methyl]xanthine is reduced with hydrazine hydrate or hydrogen gas in the presence of a palladium catalyst to yield 3-[2-(4-aminophenyl)ethyl]-1-propyl-8-[(1H-tetrazol-5-yl)methyl]xanthine.

EXAMPLE 9

Synthesis of 8-(2-Acetaminobenzyl)-3-[2-(4-aminophenyl)ethyl]-1-propylxanthine

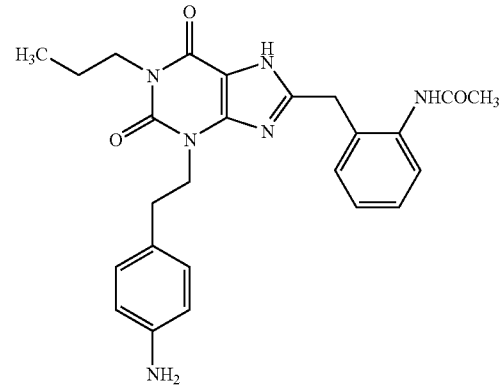

By the method of Example 2, 2-(acetamino)phenylacetic acid is reacted with 5,6-diamino-1-[2-(4-nitrophenyl)ethyl]-3-propyluracil (6) to yield 8-(2-acetaminobenzyl)-3-[2-(4-nitrophenyl)ethyl]-1-propylxanthine. By methods well known in the art, 8-(2-acetaminobenzyl)-3-[2-(4-nitrophenyl)ethyl]-1-propylxanthine is reduced with hydrazine hydrate or hydrogen gas in the presence of a palladium catalyst to yield 8-(2-acetaminobenzyl)-3-[2-(4-aminophenyl)ethyl]-1-propylxanthine.

EXAMPLE 10

Synthesis of 3-[2-(4-Aminophenyl)ethyl]-1-propyl-8-(4-sulfonoxybenzyl)xanthine

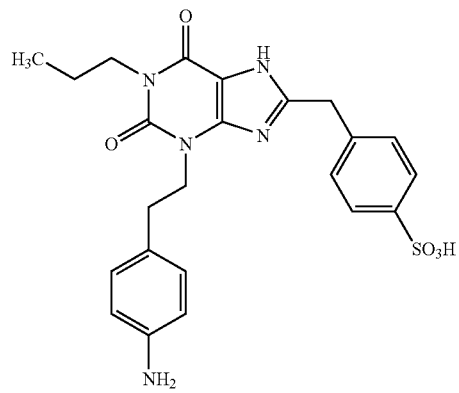

By the method of Example 2, 4-sulfonoxyphenylacetic acid is reacted with 5,6-diamino-1-[2-(4-nitrophenyl)ethyl]-3-propyluracil (6) to yield 3-[2-(4-nitrophenyl)ethyl]-1-propyl-8-(4-sulfonoxybenzyl)xanthine. By methods well known in the art, 3-[2-(4-nitrophenyl)ethyl]-1-propyl-8-(4-sulfonoxybenzyl)xanthine is reduced with hydrazine hydrate or hydrogen gas in the presence of a palladium catalyst to yield 3-[2-(4-aminophenyl)ethyl]-1-propyl-8-(4-sulfonoxybenzyl)xanthine.

EXAMPLE 11

Synthesis of 8-(2-Aminobenzyl)-3-(2-phenylethyl)-1-propylxanthine

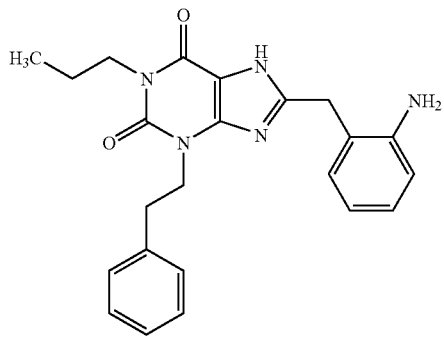

By the method of Example 2, 2-(acetamino)phenylacetic acid is reacted with 5,6-diamino-1-(2-phenylethyl)-3-propyluracil to yield 8-(2-acetaminobenzyl)-3-(2-phenylethyl)-1-propylxanthine. By methods well known in the art, 8-(2-acetaminobenzyl)-3-(2-phenylethyl)-1-propylxanthine is hydrolyzed with base to yield 8-(2-aminobenzyl)-3-(2-phenylethyl)-1-propylxanthine. In turn, 5,6-diamino-1-(2-(phenylethyl)-3-propyluracil is made by the synthetic methods of Example 1, starting with phenethylamine hydrochloride.

EXAMPLE 12

Synthesis of 8-Benzyl-3-[2-(3-carboxyphenyl)ethyl]-1-propylxanthine

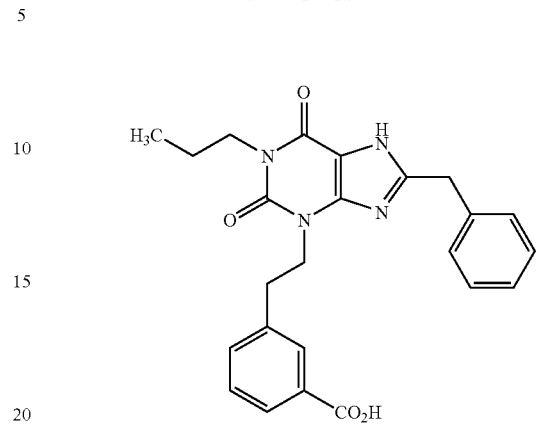

By the method of Example 2, phenylacetic acid is reacted with 5,6-diamino-1-[2-(3-carboxyphenyl)ethyl]-3-propyluracil to yield 8-benzyl-3-[2-(3-carboxyphenyl)ethyl]-1-propylxanthine. In turn, 5,6-diamino-1-[2-(3-carboxyphenyl)ethyl]-3-propyluracil is made by the synthetic methods of Example 1, starting with 3-carboxyphenethylamine.

EXAMPLES 13–18

Examples 13–18 describe the synthesis of the following compounds:

Example 13

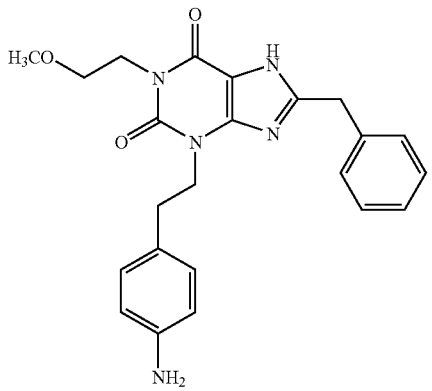

Example 14

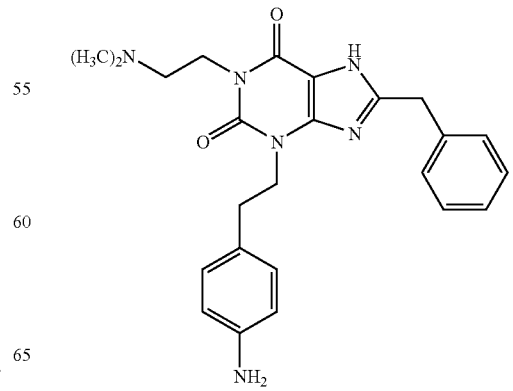

-continued

Example 15

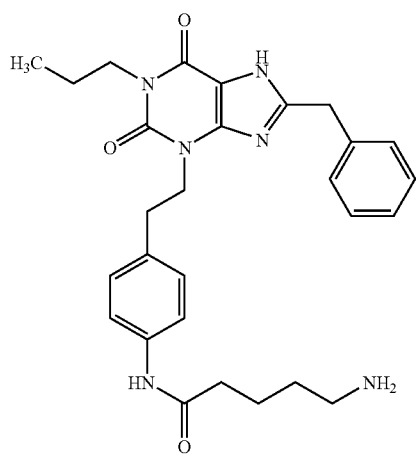

Example 16

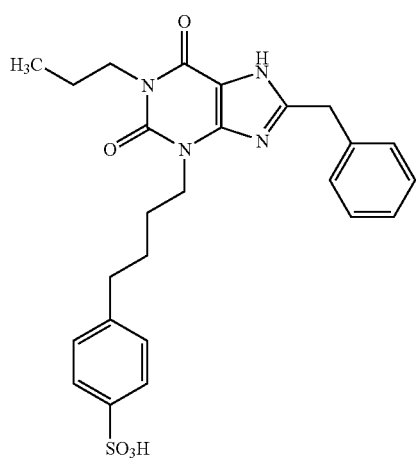

Example 17

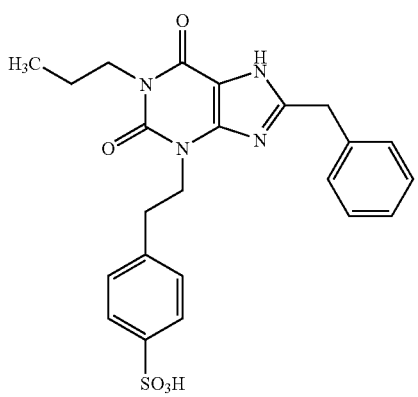

-continued

Example 18

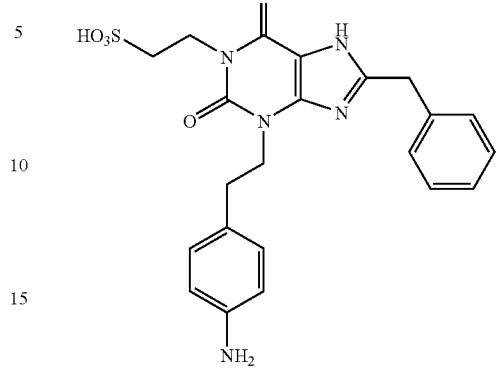

EXAMPLE 13

Synthesis of 3-[2-(4-Aminophenyl)ethyl]-8-benzyl-1-(3-methoxypropyl)xanthine

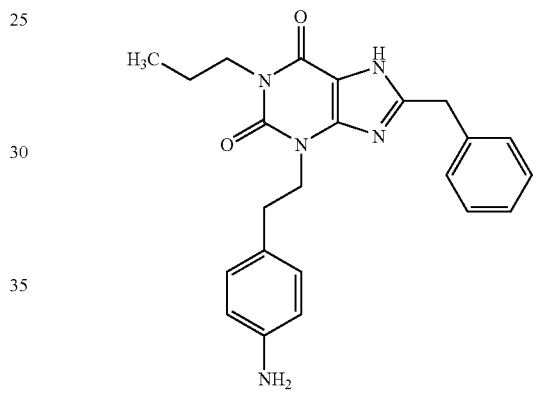

By methods well known in the art 3-methoxypropyl isocyanate is converted into 8-benzyl-3-[2-(4-nitrophenyl)ethyl]-1-(3-methoxypropyl)xanthine, which in turn, is reduced with hydrazine hydrate or hydrogen gas in the presence of a palladium catalyst to yield 3-[2-(4-aminophenyl)ethyl]-8-benzyl-1-(3-methoxypropyl)xanthine.

EXAMPLE 14

Synthesis of 3-[2-(4-Aminophenyl)ethyl]-8-benzyl-1-(3-dimethylamino)propylxanthine

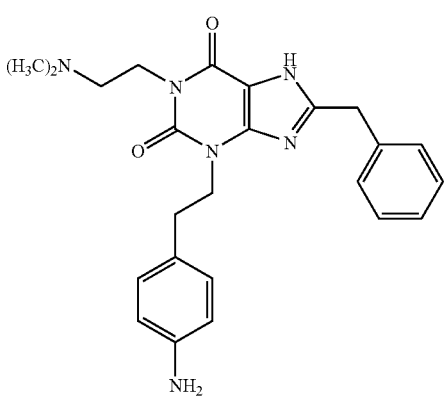

By methods well known in the art 3-dimethylaminopropyl isocyanate is converted into 8-benzyl-3-[2-(4-nitrophenyl)ethyl]-1-(3-dimethylaminopropyl)xanthine, which in turn, is reduced with hydrazine hydrate or hydrogen gas in the presence of a palladium catalyst to yield 3-[2-(4-aminophenyl)ethyl]-8-benzyl-1-(3-dimethylaminopropyl) xanthine.

EXAMPLE 15

Synthesis of 3-[2-[4-(6-Aminohexanoyl)aminophenyl]ethyl]-8benzyl-1-propylxanthine

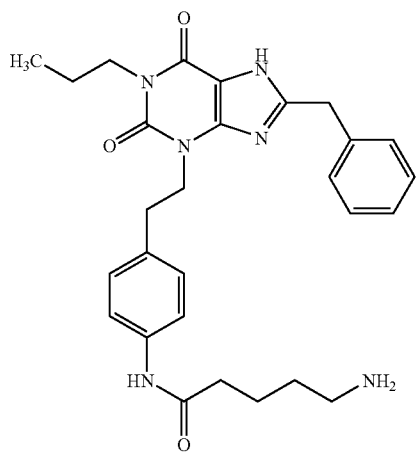

By methods well known in the art, 3-[2-(4-aminophenyl)ethyl]-8-benzyl-1-propylxanthine is reacted with 6-aminohexanoic acid and a coupling agent such as 1-(3-dimethylaminopropyl)-3-ethylcarbodiimide hydrochloride (EDC) to yield 3-[2-[4-(6-aminohexanoyl)aminophenyl]ethyl]-8-benzyl-1-propylxanthine.

EXAMPLE 16

Synthesis of 8-Benzyl-1-propyl-3-[4-(4-sulfonoxyphenyl)butyl]xanthine

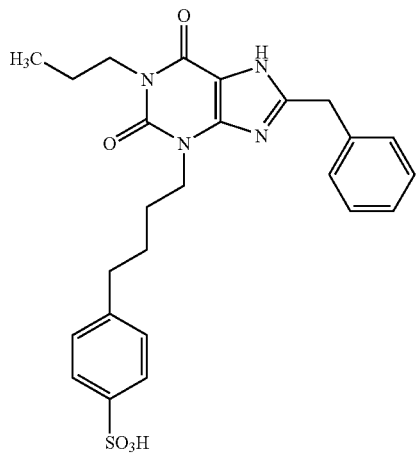

By the method of Example 2, phenylacetic acid is reacted with 5,6-diamino-1-[4-(4-sulfonoxyphenyl)butyl]-3-propyluracil to yield 8-benzyl-1-propyl-3-[4-(4-sulfonoxyphenyl)butyl]xanthine. In turn, 5,6-diamino-3-propyl-1-[4-(4-sulfonoxyphenyl)butyl]-3-uracil is made by the synthetic methods of Example 1, starting with n-propyl isocyanate and 4-(4-sulfonoxyphenyl)butylamine.

EXAMPLE 17

Synthesis of 8-Benzyl-1-propyl-3-[2-(4-sulfonoxyphenyl)ethyl]xanthine

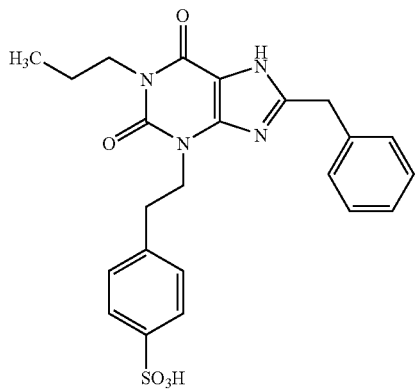

By the method of Example 2, phenylacetic acid is reacted with 5,6-diamino-1-[2-(4-sulfonoxyphenyl)ethyl]-3-propyluracil to yield 8-benzyl-1-propyl-3-[2-(4-sulfonoxyphenyl)ethyl]xanthine. In turn, 5,6-diamino-1-[2-(4-sulfonoxyphenyl)ethyl]-3-propyluracil is made by the synthetic methods of Example 1, starting with 4-sulfonoxyphenethylamine.

EXAMPLE 18

Synthesis of 3-[2-(4-Aminophenyl)ethyl]-8-benzyl-1-(3-sulfonoxypropyl)xanthine

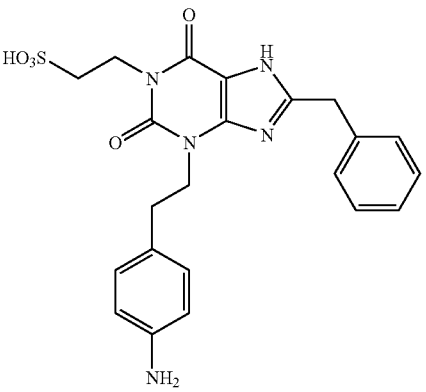

By methods well known in the art a protected 3-sulfonoxypropyl isocyanate is converted into 8-benzyl-3-[2-(4-nitrophenyl)ethyl]-1-(3-sulfonoxypropyl)xanthine, which in turn, is reduced with hydrazine hydrate or hydrogen gas in the presence of a palladium catalyst to yield 3-[2-(4-aminophenyl)ethyl]-8-benzyl-1-(3-sulfonoxypropyl)xanthine.

In the specification above, there have been disclosed typical preferred embodiments of the invention and, That which is claimed is:

1. A compound of formula (I):

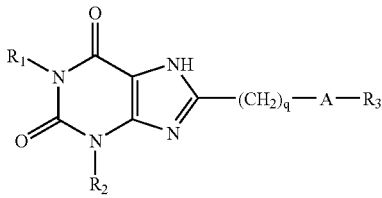

wherein:
A is a 5- or 6-membered heteroaromatic ring containing 1 to 4 heteroatoms selected from the group consisting of N, O, and S;
$R_2$ is of the formula (i):

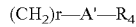  (i)

wherein:
A' is a 6-membered aromatic ring or heteroaromatic ring containing 1 to 4 nitrogen atoms;
r is an integer ranging from 1 to 20;
$R_4$ is selected from the group consisting of H; $NH_2$; $(CH_2)_sOH$, wherein s is an integer ranging from 1 to 8; $R_{14}COOH$, wherein $R_{14}$ is an alkylene or alkylidene group having 1 to 8 carbon atoms; halo, $NHR_8$, $NR_8R_9$, $NHCOR_8$, $NR_8COR_9$, $SO_3H$ and $PO_3H_2$;
$R_3$ is selected from the group consisting of H, $NH_2$, $R_{15}COOH$, wherein $R_{15}$ is an alkylene or alkylidene group having 1 to 8 carbon atoms, and $(CH_2)_tOH$, wherein t is an integer ranging from 1 to 8; halo, $NHR_8$, $NR_8R_9$, $NHCOR_8$, $NR_8COR_9$, $SO_3H$ and $PO_3H_2$;
q is an integer ranging from 1 to 8; and
$R_1$ is a $C_1$–$C_8$ alkanyl group, $C_2$–$C_8$-alkenyl- or C2–$C_8$-alkynyl- group which is optionally substituted by —CN, —$CH_2NR_6R_7OH$, —$OR_8$, —$NR_6R_7$, —NHCOR_8$, $NHCONR_6R_7$, halogen, —$OCOR_8$, —$OCH_2COOH$, —$OCH_2COOR_8$, —$SO_2R_5$, —S—$R_5$, —$OCH_2$—$CONR_6R_7$, —$OCH_2CH_2OH$, —$SO_2$—$CH_2$—$CH_2$—O—$COR_8$, —$OCH_2$—$CH_2$—$NR_6R_7$, —$SO_2$—$CH_2$—$CH_2$—OH, —$CONHSO_2R_8$, —$CH_2CONHSO_2R_8$, —$OCH_2CH_2OR_8$, —COOH, —$COOR_8$, —$CONR_6R_7$, —CHO, —$SR_8$, —$SOR_8$, —$SO_2R_8$, —$SO_3H$, —$PO_3H_2$, —$SO_2NR_6R_7$, —$OCH_2$—$CH_2OCOR_8$, —CH=NOH, —CH=$NOR_8$, —$COR_9$, —CH(OH)$R_9$, —CH(OR_8)_2$, —CH=CH—$R_{10}$, —$OCONR_6R_7$,
$R_5$ is $C_1$–$C_4$-alkyl, optionally substituted by OH, $OCOR_8$, $NH_2$, $NR_6R_7$ or $NHCOR_8$,
$R_6$ and $R_7$ are each independently hydrogen, an optionally substituted $C_{3-6}$-cycloalkyl group, a branched or unbranched alkyl-, alkenyl- or alkynyl group having up to 10 carbon atoms, which may optionally be substituted by hydroxy, phenyl, substituted phenyl, amino, or it denotes —$(CH_2)_m$—$NHCOOR_8$ wherein m=1, 2, 3 or 4;
$R_8$ is hydrogen, $C_1$–$C_8$-alkyl or $C_2$–$C_8$-alkenyl or $C_2$–$C_8$-alkynyl optionally substituted with $CO_2H$, a benzyl- or phenyl- group, which is optionally mono- or polysubstituted by $OCH_3$;
$R_9$ is $C_1$–$C_8$-alkyl or $C_2$–$C_8$-alkenyl or $C_2$–$C_8$-alkynyl optionally substituted with $CO_2H$, optionally substituted phenyl, optionally substituted benzyl, $C_3$–$C_6$-cycloalkyl, and
$R_{10}$ is —$COOR_8$, —$CH_2OR_8$, —$CONR_6R_7$, hydrogen, $C_1$–$C_3$-alkyl, optionally substituted phenyl, —$CH_2NR_6R_7$;
and pharmaceutically acceptable salts, and prodrugs thereof.

2. The compound of claim 1, wherein at least one of $R_3$ and $R_4$ is independently selected from the group consisting of $SO_3H$ and $PO_3H_2$.

3. The compound of claim 1, wherein $R_1$ is a $C_1$–$C_8$ alkanyl group, $C_2$–$C_8$-alkenyl group or $C_2$–$C_8$ alkynyl group which is optionally substituted by $NR_6R_7$, —$SO_3H$, or —$PO_3H_2$.

4. The compound of claim 1, wherein A is selected from the group selected from the group consisting of pyridyl, thiophenyl, thiazolyl, and tetrazolyl.

5. The compound of claim 1, wherein A' is phenyl.

6. The compound of claim 1, wherein:
$R_1$ is a $C_1$–$C_8$ alkanyl group, $C_2$–$C_8$-alkenyl group or $C_2$–$C_8$ alkynyl group which is optionally substituted by $NR_6R_7$ or —$SO_3H$;
A is selected from the group selected from the group consisting of pyridyl, thiophenyl, thiazolyl, and tetrazolyl; and
A' is phenyl.

7. The compound of claim 6, wherein at least one of $R_3$ and $R_4$ is independently selected from the group consisting of $SO_3H$ and $PO_3H_2$.

8. The compound of claim 1, wherein said compound is selected from the group consisting of:
3-[2-(4-Aminophenyl)ethyl]-1-propyl-8-[(3-pyridyl)methyl]xanthine;
3-[2-(4-Aminophenyl)ethyl]-1-propyl-8-[(4-thiazolyl)methyl]xanthine;
3-[2-(4-Aminophenyl)ethyl]-1-propyl-8-[(thiophen-2-yl)methyl]xanthine;
3-[2-(4-Aminophenyl)ethyl]-1-propyl-8-[(1H-tetrazol-5-yl)methyl]xanthine;
and pharmaceutically acceptable salts, and prodrugs thereof.

9. A composition comprising a compound of claim 1 in a pharmaceutically acceptable carrier.

10. A compound of formula (I):

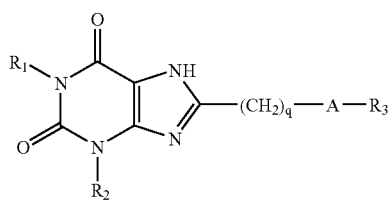

wherein:
A is a 5- or 6-membered aromatic ring;
$R_2$ is of the formula (i):

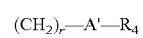  (i)

wherein:
A' is a 6-membered aromatic ring or a heteroaromatic ring containing 1 to 4 nitrogen atoms;
r is an integer ranging from 1 to 20;

$R_4$ is selected from the group consisting of $NH_2$, halo, $NHR_8$, $NR_8R_9$, $NHCOR_8$, $NR_8COR_9$, $SO_3H$ and $PO_3H_2$;

$R_3$ is selected from the group consisting of H, $NH_2$, $R_{15}COOH$, wherein $R_{15}$ is an alkylene or alkylidene group having 1 to 8 carbon atoms, and $(CH_2)_tOH$, wherein t is an integer ranging from 1 to 8; halo, $NHR_8$, $NR_8R_9$, $NHCOR_8$, $NR_8COR_9$, $SO_3H$ and $PO_3H_2$;

q is an integer ranging from 1 to 8; and $R_1$ is a $C_1$–$C_8$ alkanyl- group, $C_2$–$C_8$-alkenyl-, or $C_2$–$C_8$-alkynyl- group which is optionally substituted by —CN, —$CH_2NR_6R_7OH$, —$OR_8$, —$NR_6R_7$, —NHCOR$_8$, —$NHCONR_6R_7$, halogen, —$OCOR_8$, —$OCH_2COOH$, —$OCH_2COOR_8$, —$SO_2R_5$, —S—$R_5$, —$OCH_2$—$CONR_6R_7$, —$OCH_2CH_2OH$, —$SO_2$—$CH_2$—$CH_2$—O—$COR_8$, —$OCH_2$—$CH_2$—$NR_6R_7$, —$SO_2$—$CH_2$—$CH_2$—OH, —$CONHSO_2R_8$, —$CH_2CONHSO_2R_8$, —$OCH_2CH_2OR_8$, —COOH, —$COOR_8$, —$CONR_6R_7$, —CHO, —$SR_8$, —$SOR_8$, —$SO_2R_8$, —$SO_3H$, —$PO_3H_2$, —$SO_2NR_6R_7$, —$OCH_2$—$CH_2OCOR_8$, —CH=NOH, —CH=$NOR_8$, —$COR_9$, —CH(OH)$R_9$, —CH($OR_8$)$_2$, —CH=CH—$R_{10}$, —$OCONR_6R_7$, $R_5$ is $C_1$–$C_4$-alkyl, optionally substituted by OH, $OCOR_8$, $NH_2$, $NR_6R_7$ or $NHCOR_8$, $R_6$ and $R_7$ are each independently hydrogen, an optionally substituted $C_{3-6}$-cycloalkyl group, a branched or unbranched alkyl-, alkenyl- or alkynyl group having up to 10 carbon atoms, which may optionally be substituted by hydroxy, phenyl, substituted phenyl, amino, or it denotes —(CH$_2$)$_m$—$NHCOOR_8$ wherein m=1, 2, 3 or 4;

$R_8$ is hydrogen, $C_1$–$C_8$-alkyl or $C_2$–$C_8$-alkenyl or $C_2$–$C_8$-alkynyl optionally substituted with $CO_2H$, a benzyl- or phenyl- group, which is optionally mono- or polysubstituted by $OCH_3$;

$R_9$ is $C_1$–$C_8$-alkyl or $C_2$–$C_8$-alkenyl or $C_2$–$C_8$-alkynyl optionally substituted with $CO_2H$, optionally substituted phenyl, optionally substituted benzyl, $C_3$–$C_6$-cycloalkyl, and $R_{10}$ is —$COOR_8$, —$CH_2OR_8$, —$CONR_6R_7$, hydrogen, $C_1$–$C_3$-alkyl, optionally substituted phenyl, —$CH_2NR_6R_7$;

and pharmaceutically acceptable salts, and prodrugs thereof.

11. The compound of claim 10, wherein A is phenyl.

12. The compound of claim 10, wherein A' is phenyl.

13. The compound of claim 10, wherein:
A is phenyl;
A' is phenyl;
r is 2;
$R_4$ is selected from the group consisting of $NH_2$, $NHCOR_8$, and $SO_3H$;
$R_3$ is selected from the group consisting of H, $NH_2$, halo, $SO_3H$, and $NHCOR_8$;
q is 1; and
$R_1$ is a $C_1$–$C_8$ alkanyl group optionally substituted by —$OR_8$, —$NR_6R_7$, or —$SO_3H$.

14. The compound of claim 10, wherein said compound is selected from the group consisting of:
3-[2-(4-Aminophenyl)ethyl]-8-benzyl-1-propyixanthine;
3-[2-(4-Aminophenyl)ethyl]-1-propyl-8-(4-sulfobenzyl)xanthine;
3-[2-(4-Aminophenyl)ethyl]-8-benzyl-1-(3-methoxypropyl)xanthine;
3-[2-(4-Aminophenyl)ethyl]-8-benzyl-1-(3-dimethylamino)propylxanthine;
3-[2-[4-(6-Aminohexanoyl)aminophenyl]ethyl]-8-benzyl-1-propyixanthine;
8-Benzyl-1-propyl-3-[4-(4-sulfophenyl)butyl]xanthine;
8-Benzyl-1-propyl-3-[2-(4-sulfophenyl)ethyl]xanthine;
3-[2-(4-Aminophenyl)ethyl]-8-benzyl-1-(3-sulfopropyl)xanthine;
3-[2-(4-Aminophenyl)ethyl]-8-(4-fluorobenzyl)-1-propyixanthine;
8-(2-Acetaminobenzyl)-3-[2-(4-aminophenyl)ethyl]-1-propyixanthine;
8-(2-Aminobenzyl)-3-(2-phenylethyl)-1-propylxanthine;
3-[2-(4-Aminophenyl)ethyl]-8-benzyl-1-(8-sulfooctyl)xanthine;
3-[2-(4-Aminophenyl)ethyl]-8-benzyl-1-(5-sulfopentyl)xanthine;
3-[2-(4-Aminophenyl)ethyl]-8-benzyl-1-(5-sulfopentyl)xanthine; and
pharmaceutically acceptable salts, and prodrugs thereof.

15. A composition comprising a compound of claim 10 in a pharmaceutically acceptable carrier.

16. A compound selected from the group consisting of:
8-Benzyl-3-[2-(3-carboxyphenyl)ethyl]-1-propyixanthine;
3-[2-(2-carboxyphenyl)ethyl]-8-(3-fluorobenzyl)-1-propyixanthine;
3-[2-(2-carboxyphenyl)ethyl]-8-(3-nitrobenzyl)-1-propylxanthine;
3-[2-(2-carboxyphenyl)ethyl]-1-propyl-8-[(2-pyridyl)methyl]xanthine; and
3-[2-(2-carboxyphenyl)ethyl]-1-propyl-8-[(2-pyridyl)methyl]xanthine;
and pharmaceutically acceptable salts and prodrugs thereof.

17. A composition comprising a compound of claim 16 in a pharmaceutically acceptable carrier.

* * * * *

UNITED STATES PATENT AND TRADEMARK OFFICE
CERTIFICATE OF CORRECTION

PATENT NO. : 7,202,252 B2 Page 1 of 1
APPLICATION NO. : 10/780296
DATED : April 10, 2007
INVENTOR(S) : Wilson et al.

It is certified that error appears in the above-identified patent and that said Letters Patent is hereby corrected as shown below:

Column 13,
Line 66: "3" should read --4--

Column 30,
Line 8: "propyixanthine;" should read --propylxanthine;--
Line 16: "propyixanthine;" should read --propylxanthine;--
Line 22: "propyixanthine;" should read --propylxanthine;--
Line 24: "propyixanthine;" should read --propylxanthine;--
Line 37: "propyixanthine;" should read --propylxanthine;--
Line 39: "propyixanthine;" should read --propylxanthine;--

Signed and Sealed this

Twenty-fourth Day of July, 2007

JON W. DUDAS
*Director of the United States Patent and Trademark Office*